United States Patent [19]

Cohen et al.

[11] Patent Number: 5,023,783
[45] Date of Patent: Jun. 11, 1991

[54] EVOKED RESPONSE AUDIOMETER FOR TESTING SLEEPING SUBJECTS

[75] Inventors: Lawrence T. Cohen; Field W. Rickards, both of Melbourne, Australia

[73] Assignee: The University of Melbourne, Victoria, Australia

[21] Appl. No.: 534,356

[22] Filed: Jun. 8, 1990

Related U.S. Application Data

[63] Continuation of Ser. No. 270,042, Nov. 14, 1988, abandoned.

[30] Foreign Application Priority Data

Nov. 13, 1987 [AU] Australia .................. PI5454

[51] Int. Cl.⁵ .................. A61B 5/0484; A61B 5/12
[52] U.S. Cl. .................. 364/413.02; 128/746; 364/413.05
[58] Field of Search .............. 128/746; 364/413.02, 364/413.05

[56] References Cited

U.S. PATENT DOCUMENTS

| | | | |
|---|---|---|---|
| 4,462,411 | 7/1984 | Rickards | 128/746 |
| 4,561,449 | 12/1985 | Hu et al. | 128/746 |
| 4,576,173 | 3/1986 | Parker et al. | 128/633 |
| 4,667,683 | 5/1987 | Dugot | 128/746 |
| 4,718,094 | 1/1988 | Bahl et al. | 381/43 |
| 4,728,959 | 3/1988 | Maloney et al. | 342/457 |

OTHER PUBLICATIONS

Sekula, J. et al., "E. R. A. in Neonates", *Rev. Laryngol. Otol. Rhinol.* (France), vol. 102, Nos. 7-8, 1981, 265-267.

*Primary Examiner*—Clark J. Jablon
*Attorney, Agent, or Firm*—Nixon & Vanderhye

[57] ABSTRACT

An evoked response audiometer for sleeping subjects comprising a function generator for supplying to a sleeping patient an auditory signal consisting of a carrier frequency which is periodically modulated at frequencies in excess of 60 Hz, the frequency of modulation being varied in a generally increasing manner for auditory signals of higher frequencies such that the stimulus is frequency specific, a detector for sampling and analyzing brain potentials evoked by said signal, a low-pass filter providing a time window which samples the brain potentials for a predetermined interval to provide sets of fourier analysis samples containing amplitude and phase data in narrow bands centered on the modulation frequency and its second harmonic, a computer for analyzing the Fourier analysis samples to extract means values of the amplitudes and phase angles of the signals, and for extracting from the means values of the phase angles the probabilities that the distributions of the phase angles could have occurred by change, whereby the existence of phase locking of the brain potential signals can be determined.

18 Claims, 24 Drawing Sheets

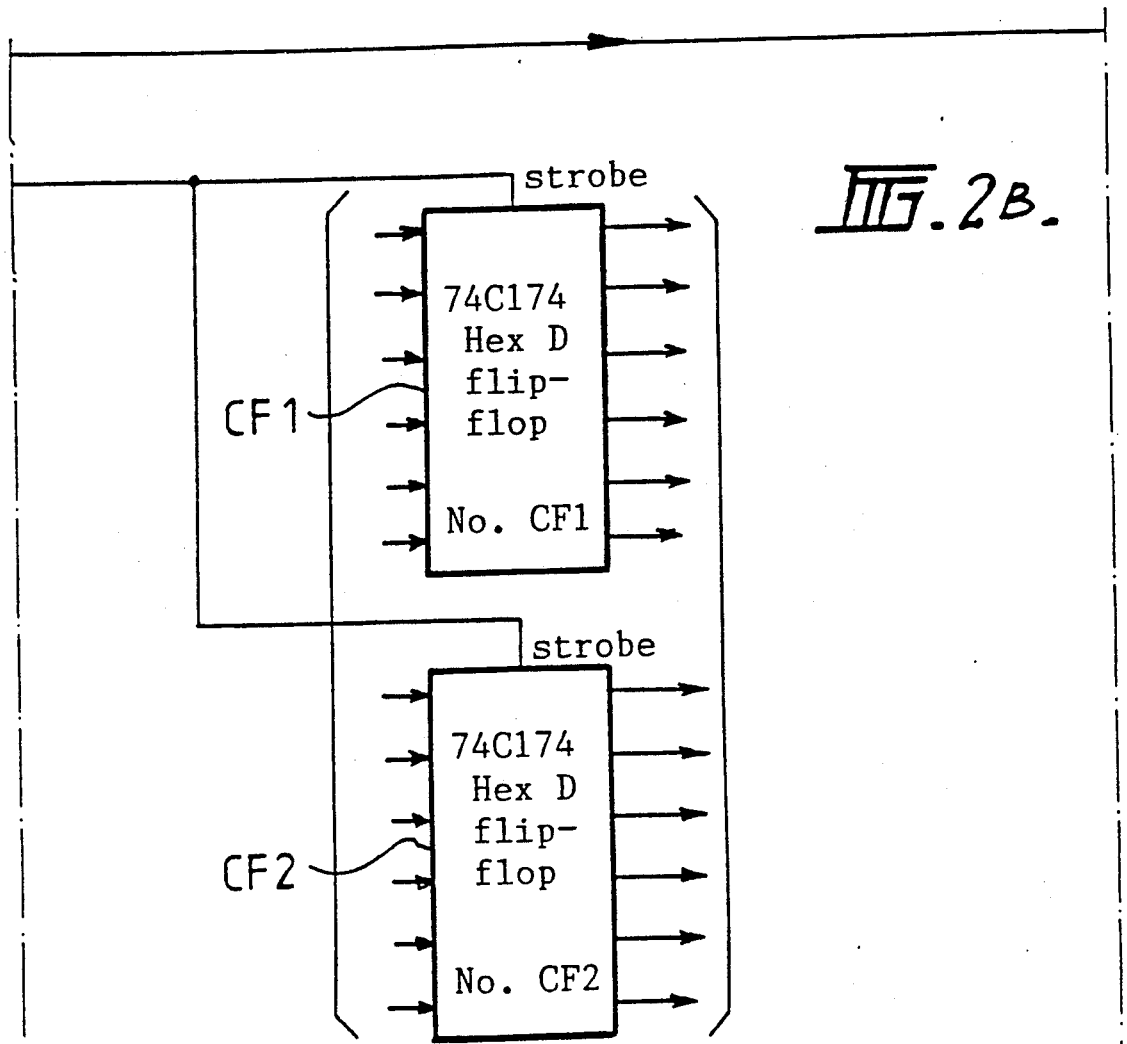
FIG. 2B.
CF data flip-flops.
Input: comp bits 1-12
Output: stored data
(There are 5 other
flip-flop pairs
corresponding to
MF,DF,DA,LA &RA )
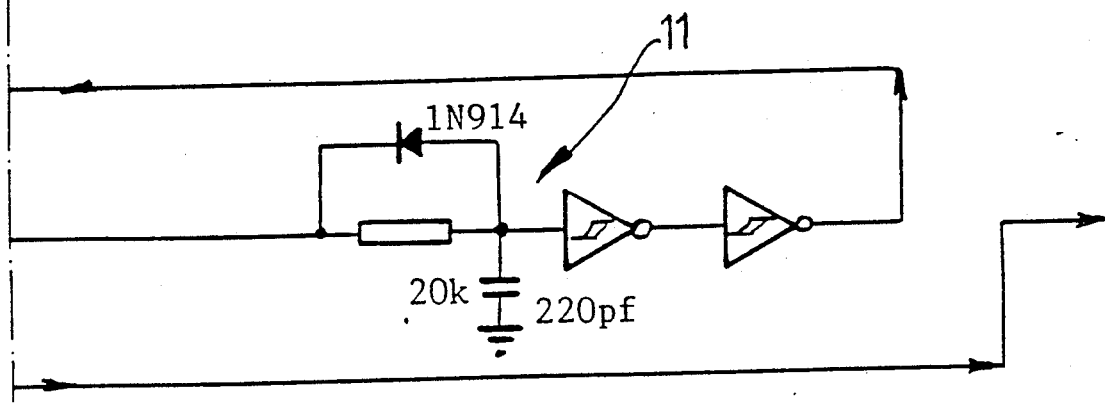

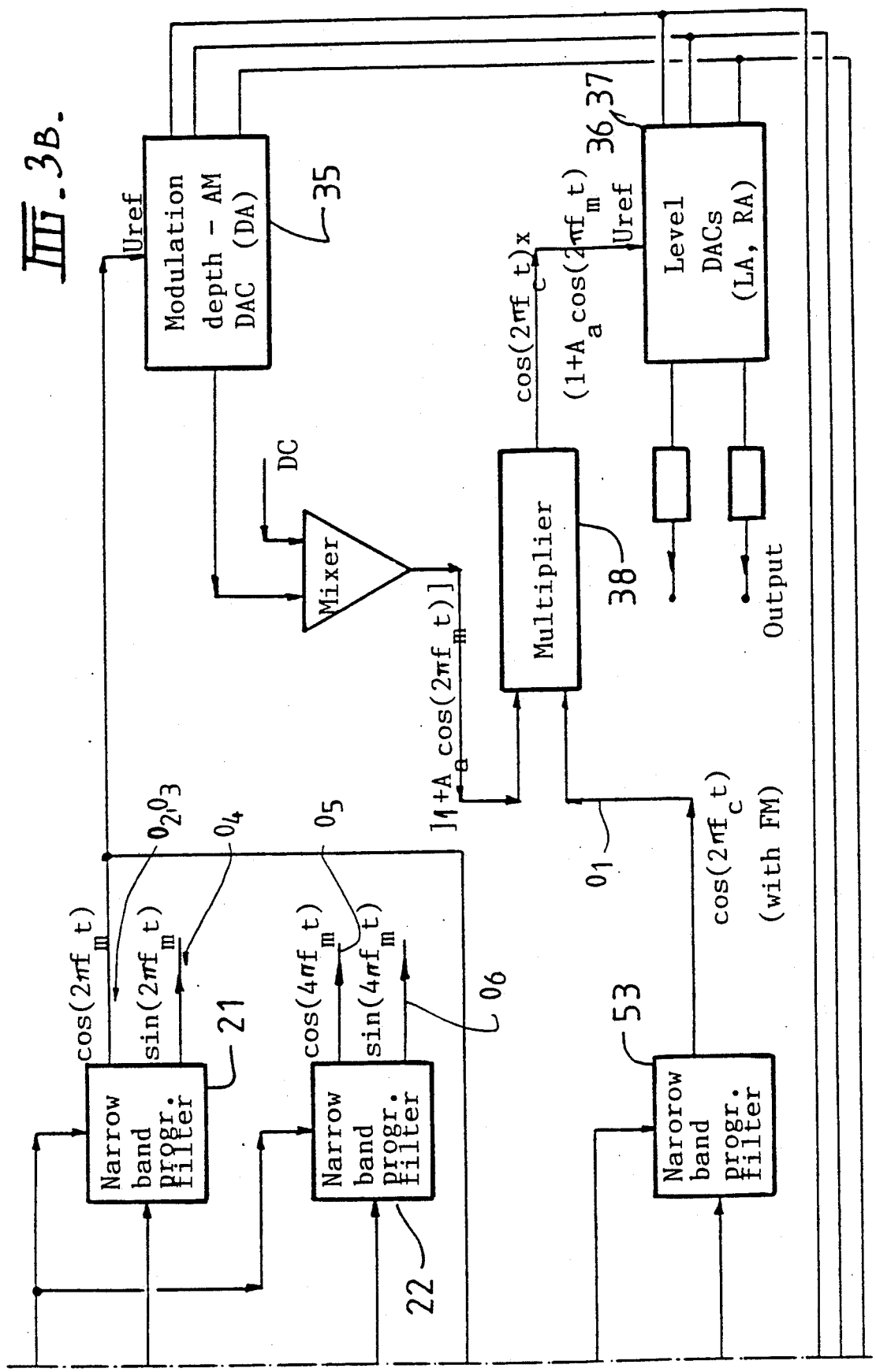

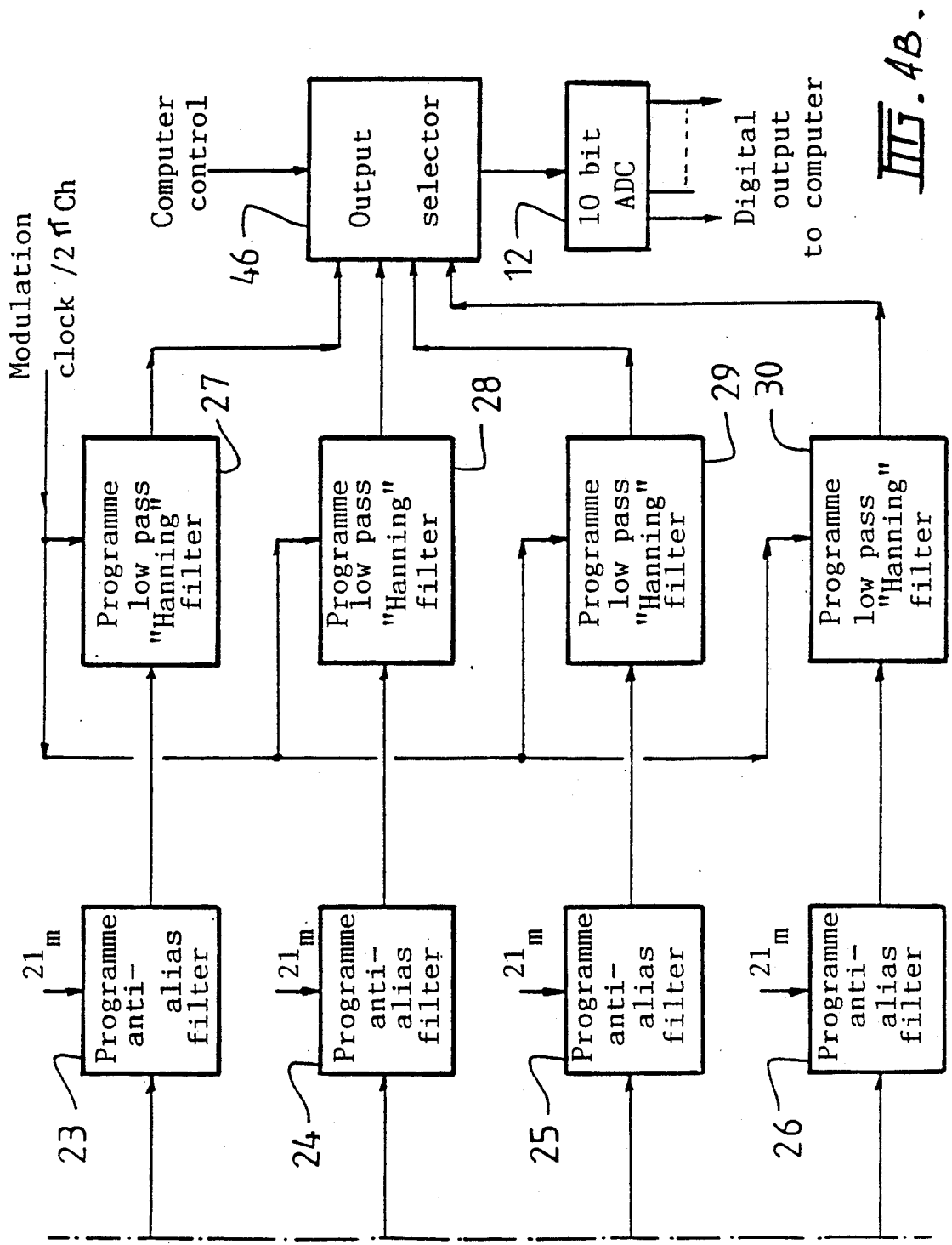

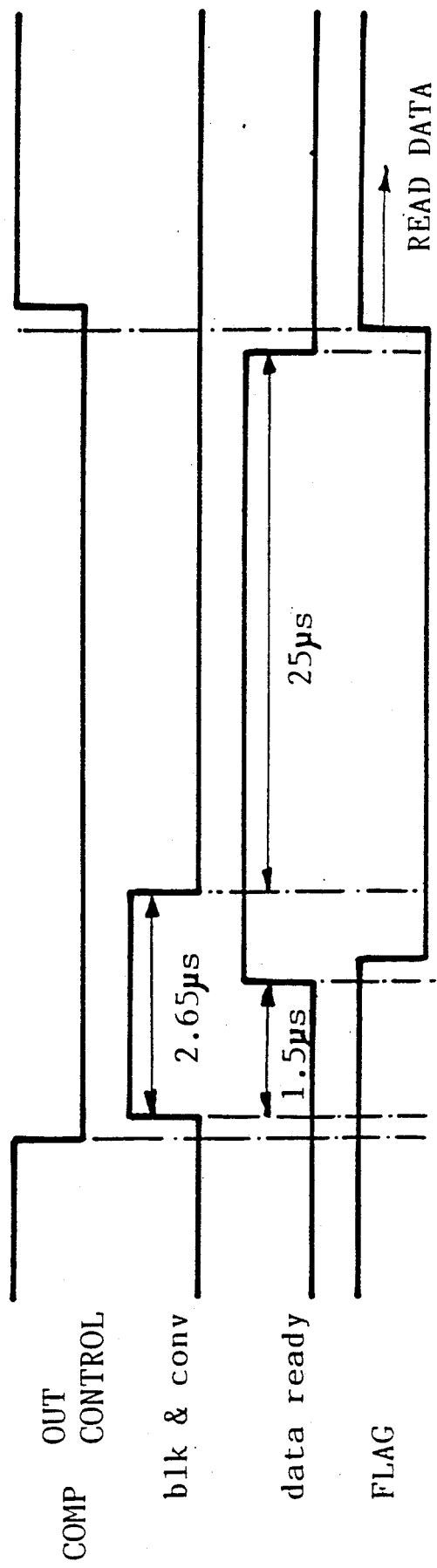

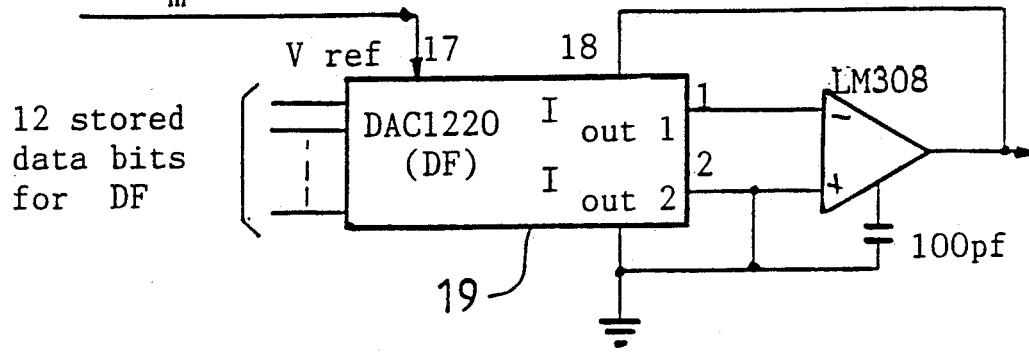
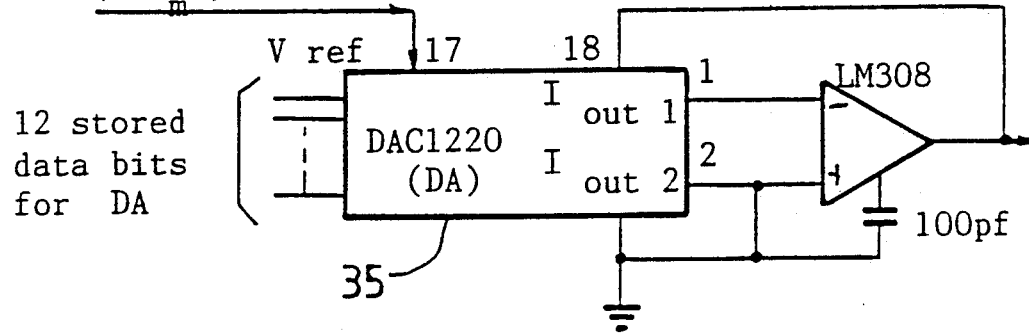
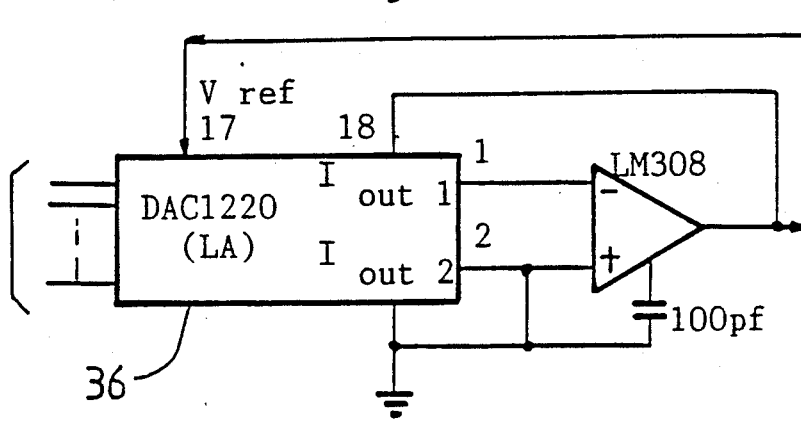
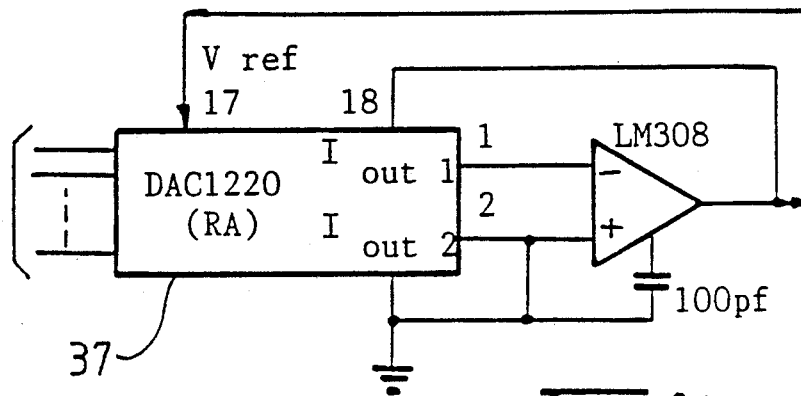
FIG. 8A.

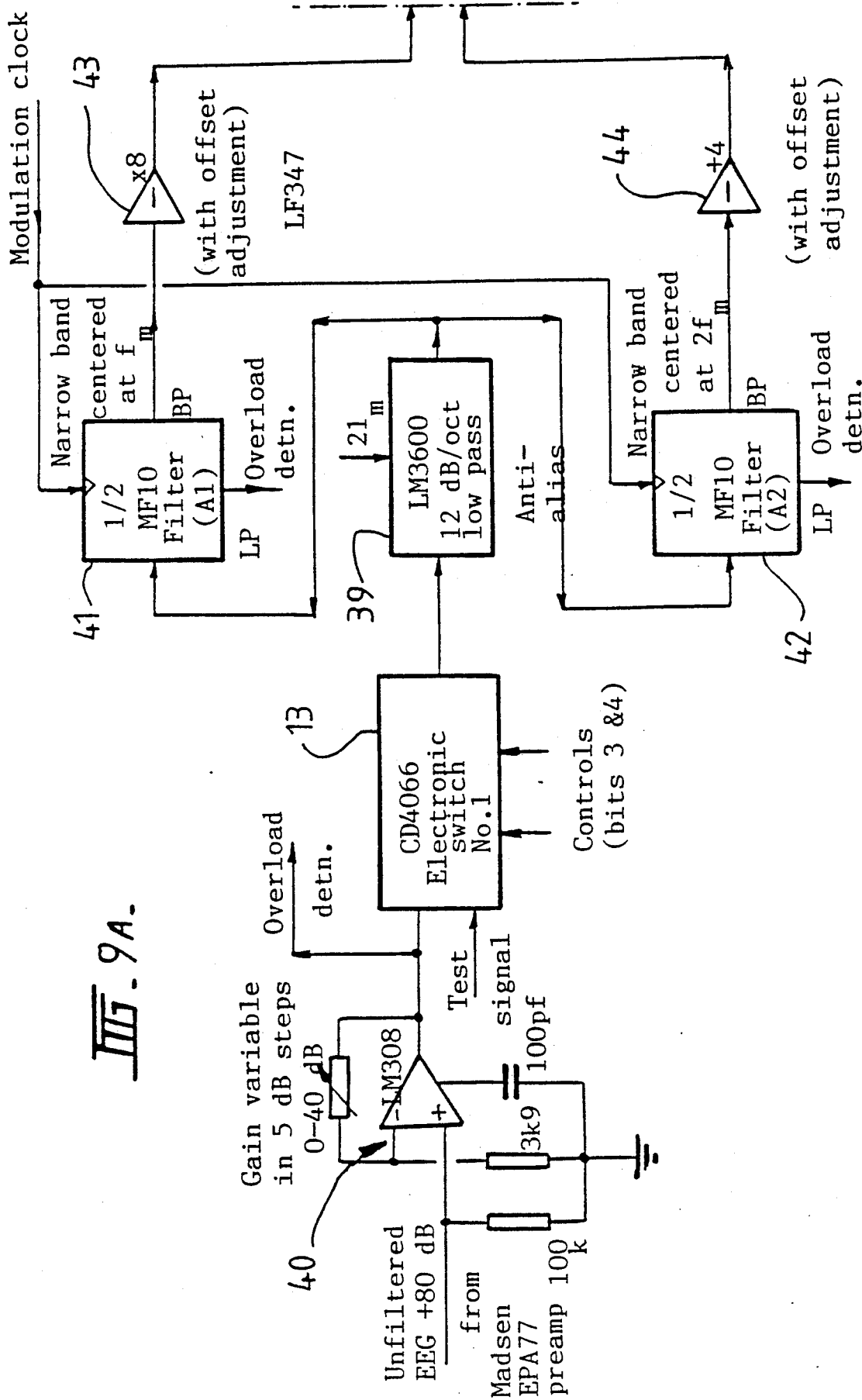

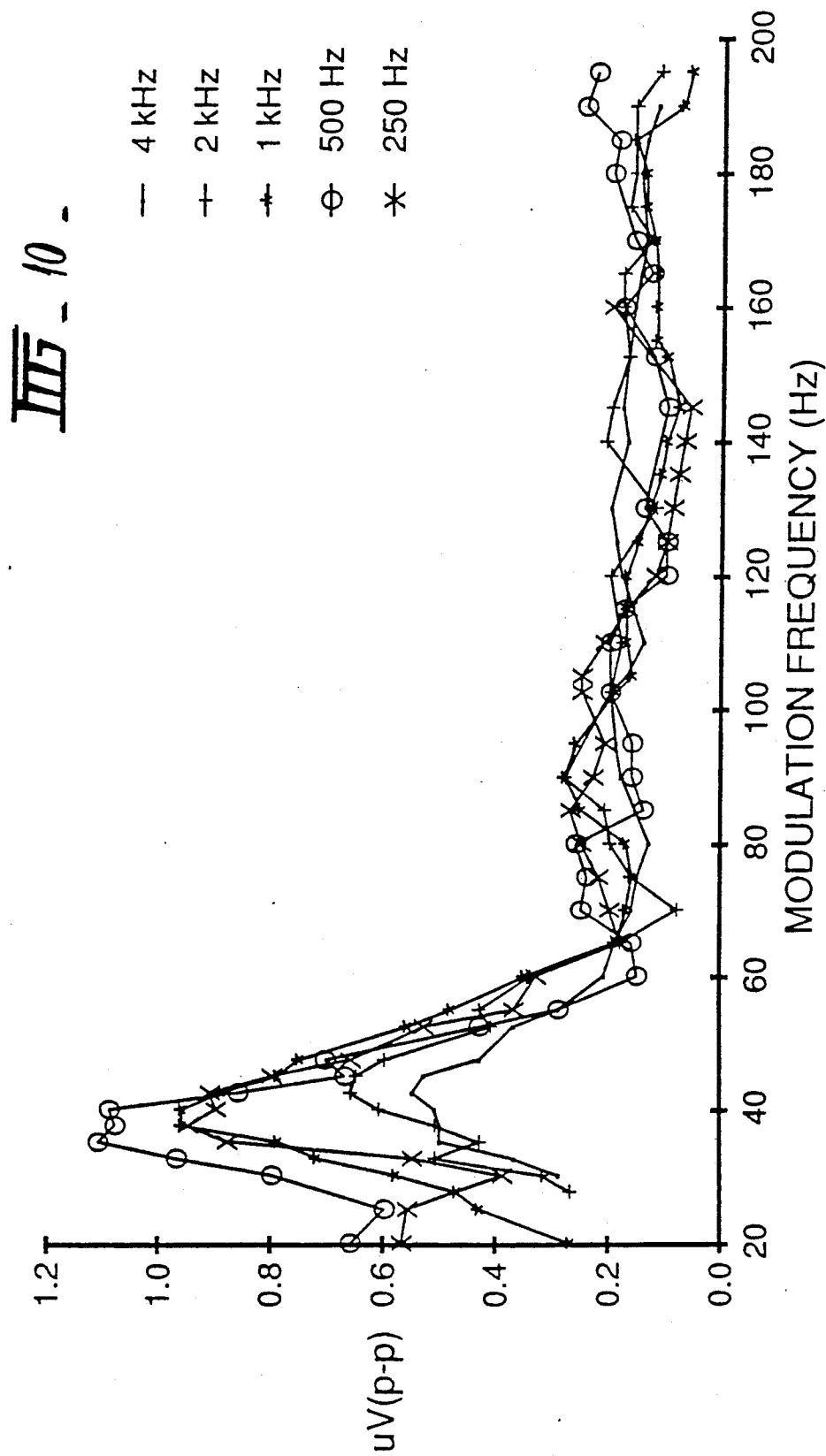

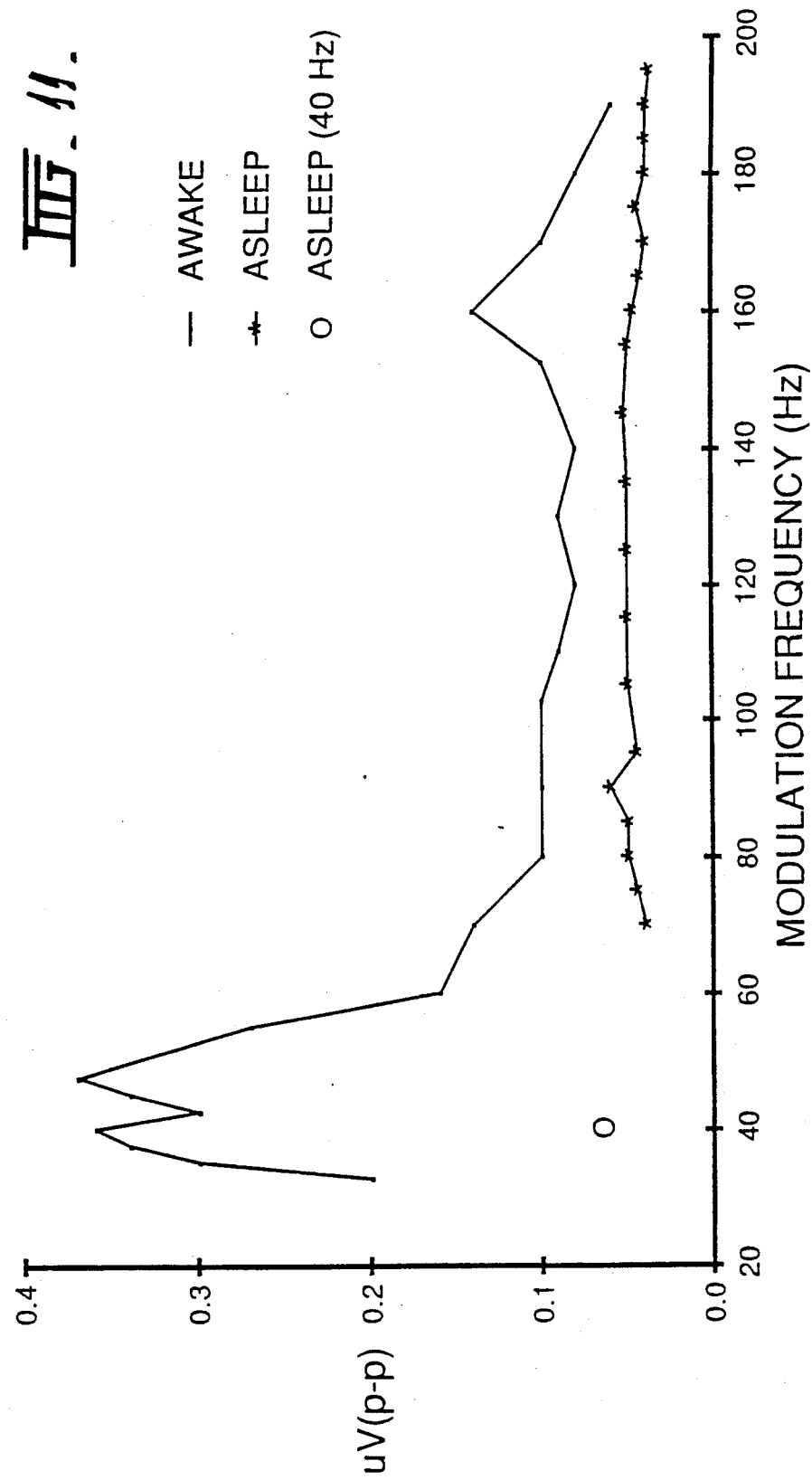

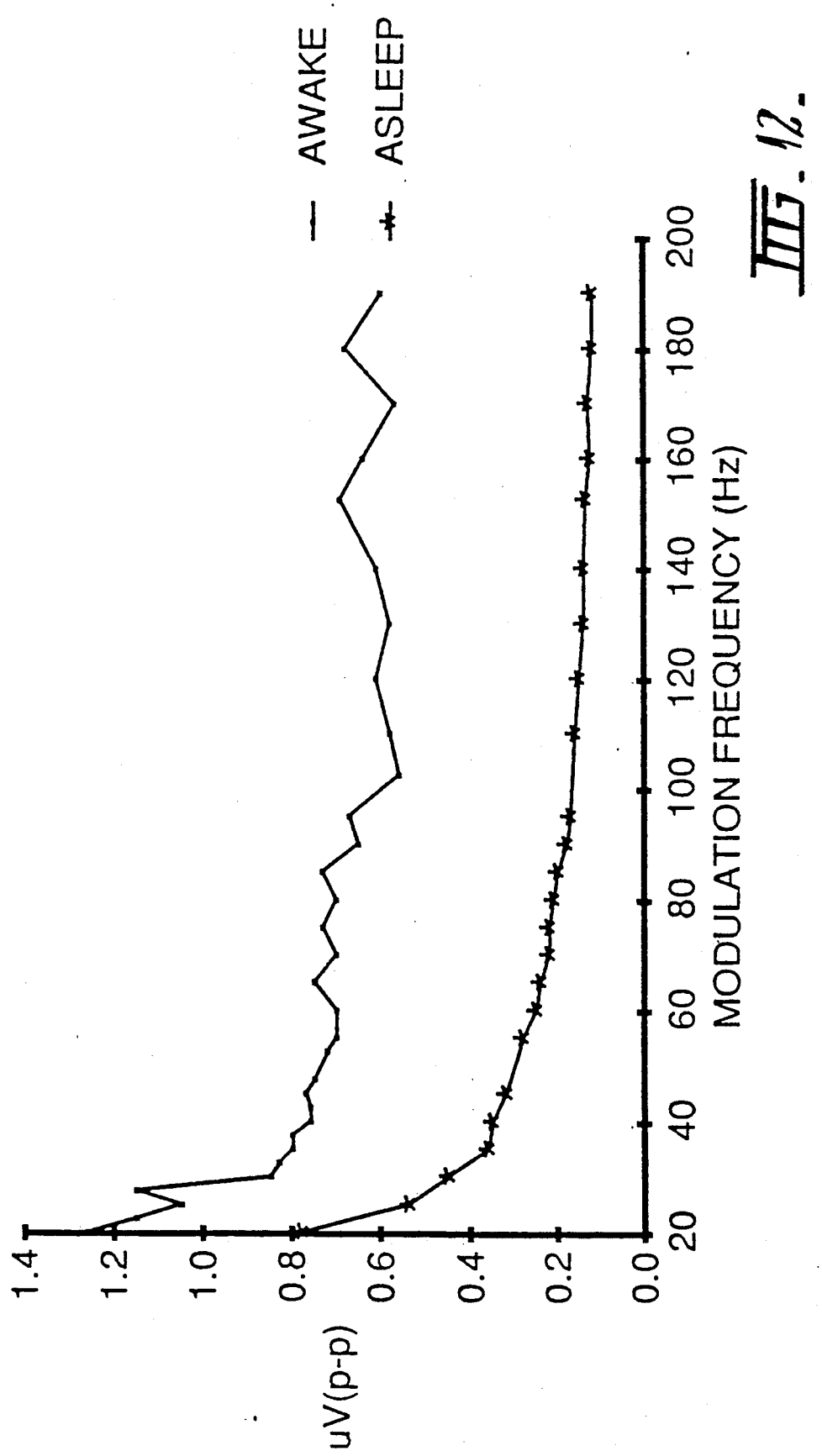

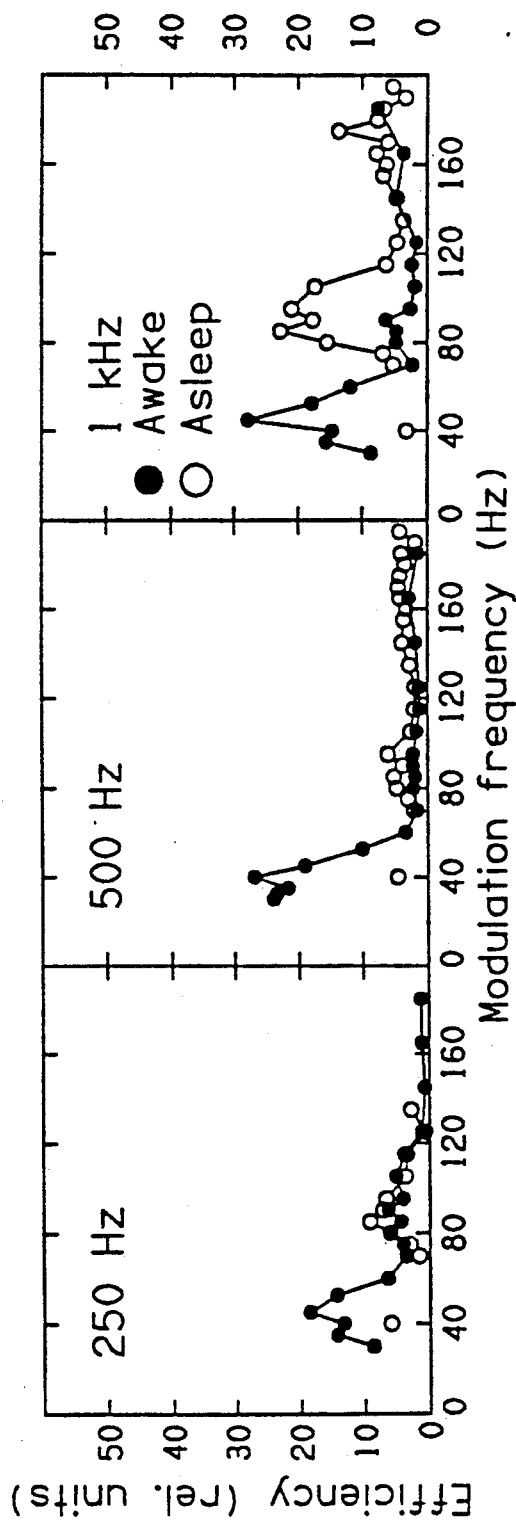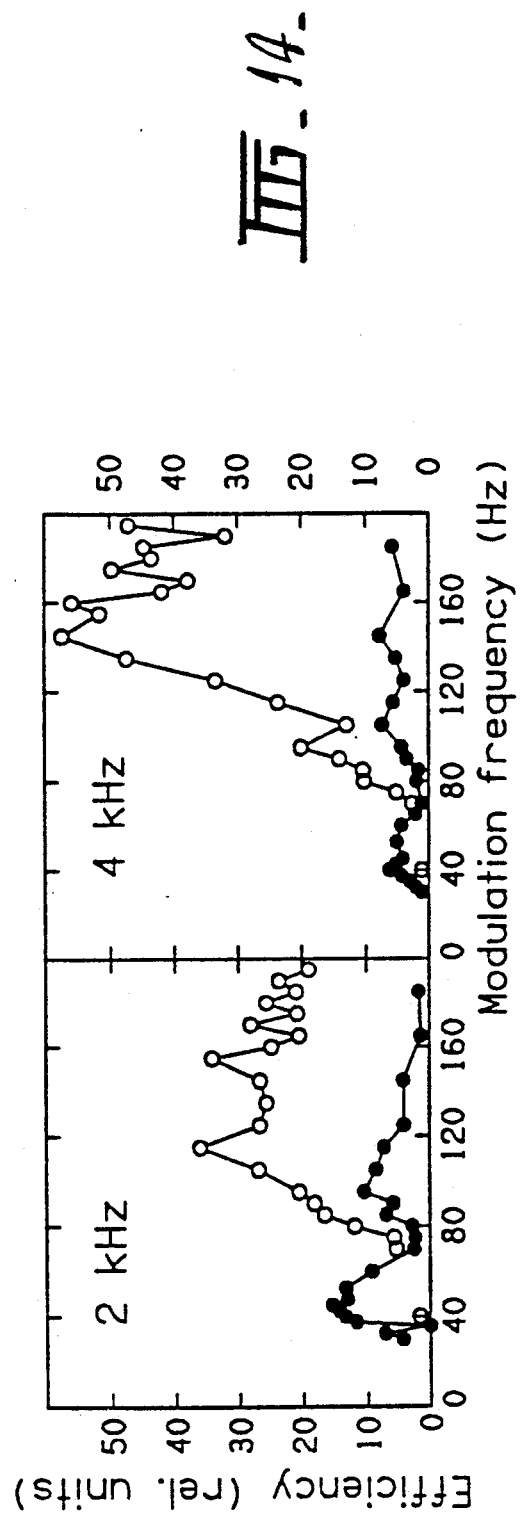
FIG. 14

EVOKED RESPONSE AUDIOMETER FOR TESTING SLEEPING SUBJECTS

This is a continuation of application Ser. No. 07/270,042, filed Nov. 14, 1988, now abandoned.

FIELD OF THE INVENTION

This invention relates to an improved evoked response audiometer to be used with sleeping subjects, with special reference to neonates, young children and mentally handicapped persons.

BACKGROUND OF THE INVENTION

The diagnosis of deafness at an early stage is most important to enable the early fitting of hearing aids and in the application of educational programs to assist language development in the hearing impaired child. Current procedures in the early diagnosis of deafness include the "Cribogram" and brainstem evoked response.

Auditory evoked potentials recorded from the scalp in humans have now been described in many studies. These potentials have been classified into three main groups. These groups are:

(i) brainstem evoked potentials which are approximately 0.5 microvolts in amplitude and occur during the first 10 milliseconds following the presentation of an abrupt sound stimulus, usually a click.

(ii) the middle latency responses which are approximately two microvolts in amplitude and occur between 7 and 50 milliseconds following the presentation of a click or tone pip and, (iii) slow responses, about 10 microvolts in amplitude, following the onset of a tone burst and have latencies between 50 and 500 milliseconds.

Currently, the brainstem potential is receiving most attention both as a neurological and an audiological tool. It does, however, have the disadvantage of using abrupt stimuli. This is necessary since this response reflects synchronous firing patterns in the auditory pathway in the brainstem. Stimuli of slower onset fail to achieve the synchrony necessary for the recording of the various peaks. As a result of this limitation only high frequency hearing information is measured.

The middle latency responses are also currently receiving attention as a measure of low frequency hearing with low frequency tone bursts being repeated forty times per second to evoke a periodic response. This response is affected by sleep and therefore has limited application in the testing of babies.

The periodic 40 Hz middle latency responses are a subgroup of the auditory steady-state evoked potentials. These are periodic responses, recorded from the scalp to a continuous periodically varying stimulus, for example an amplitude modulated tone. The periodicity of the response is the same as the period of the modulation waveform. These can be recorded over a wide range of modulation and carrier frequencies.

Several classes of subject can be tested by evoked potentials only (or most conveniently) during sleep, for example infants and young children and people with mental retardation.

Existing steady-state literature shows that for low modulation rates (less than or equal to 60 Hz) responses are variable in sleeping subjects and considerably smaller in amplitude than for the waking state.

Responses at all modulation frequencies do decrease with sleep or sedation but we have found that the background noise level of the EEG decreases dramatically at high modulation frequencies and consistent responses remain present. (see FIG. 11 and FIG. 12). This means that detection of responses in sleep can easily be performed at high modulation frequencies (greater than 60 Hz).

SUMMARY OF INVENTION AND OBJECTS

It is therefore an object of the present invention to provide an improved evoked response audiometer which will make use of the optimum modulation frequencies for steady-state evoked potential testing during sleep, to allow the efficient assessment of hearing of a variety of difficult-to-test patients. These include neonates, infants, young children and mentally retarded patients The invention provides an evoked response audiometer comprising means of supplying to the patient an auditory signal consisting of a carrier frequency which is periodically modulated (for example amplitude modulation, frequently repeating tone bursts or tone pips, frequency modulation or beats) such that the stimulus is at least substantially frequency specific, said auditory signal being presented for a sufficiently extended period of time to enable phase-locked steady-state potentials to be evoked in the brain, means for sampling the brain potential signals evoked by said signal, and means for analysing said brain potentials to determine whether phase-locking of said brain potentials to the modulated auditory signal has occurred, said auditory signal means being controlled so that said auditory signals are periodically modulated at frequencies in excess of 60 Hz, the frequency of modulation being varied in a generally increasing manner for auditory signals of higher frequencies.

In a preferred form, said frequency of modulation is about 60-115 Hz for auditory signals having frequencies less than or equal to 1.5 kHz, and said frequency of modulation is about 65-200 Hz (or more) for auditory signals having frequencies in excess of 1.5 kHz.

It should be appreciated that the modulation frequency used will depend on the frequency of the auditory signal as well as on the subject being tested As an indication of the range of modulation frequencies which may be used, the following table is provided:

| Auditory Signal | Modulation Frequency |
|---|---|
| (a) Normal sleeping neonates | |
| 500 Hz: | about 60-140 Hz, preferably 65-95 Hz, and most preferably about 72 Hz |
| 1.5 kHz: | about 60-165 Hz, preferably 75-110 Hz, and most preferably about 85 Hz |
| 4 kHz: | about 65-200 + Hz, preferably 85-110 Hz, and most preferably about 97 Hz |
| Hence, 60-165 Hz for CF < 1.5 kHz | |
| 65-200 + Hz for CF > 1.5 kHz | |
| (b) Normal sleeping adults | |
| 250 Hz: | about 70-130 Hz, preferably about 80-115 Hz, and most preferably about 85-95 Hz |
| 500 Hz: | about 70-180 Hz, preferably about 80-115 Hz, and most preferably about 85-95 Hz |
| 1 kHz: | about 70-200 Hz, preferably about 80-115 Hz, and most preferably about 95 Hz |
| 2 kHz: | about 75-200 + Hz, preferably about 85-195 Hz, and most preferably about |

-continued

| Auditory Signal | Modulation Frequency |
| --- | --- |
|  | 105-160 Hz |
| 4 kHz: | about 75-200 + Hz, preferably about 85-200 + Hz, and most preferably about 120-190 Hz |
| Hence, 70-180 Hz for CF < 1 kHz |  |
| 75-200 + Hz for CF > 1 kHz |  |

It is expected that as infants mature, their responses will become more like those of adults. Accordingly, there will be a shift of optimum MF ranges.

Thus other modulating frequencies will be determined experimentally for other types of patients.

The use of modulation frequencies in excess of 60 Hz to evoke the responses allows the most efficient detection of a response in the type of patient being tested and at the carrier frequency being used. The system may be designed to choose the optimum modulation frequency automatically, based on the type of subject and the carrier frequency used. The audiometer embodying the present invention has the advantage over prior art audiometers in that it may make use of the widest possible range of modulation types (limited only by the requirement of reasonable frequency specificity), in that it makes use of the modulation frequencies that allow most efficient detection of a response during sleep (namely those in excess of 60 Hz) and that it employs a frequency specific stimulus. It also detects a response In real-time enabling the transfer to a new stimulus automatically.

The brain potentials are preferably recorded by means of electrodes on the vertex or forehand and on the mastoids of the patient, in the preferred embodiment, the patient is presented with a band limited tone burst or a tone that is simultaneously amplitude and frequency modulated or an amplitude modulated tone. The EEG signal is Fourier analysed to extract the components at the modulation frequency and its second harmonic, as these have been found to be the predominant components of the response. The use of low-pass filters following the multiplication of the EEG signal by the modulation frequency waveform and its second harmonic provides a time "window" which samples the EEG waveform for an interval of, typically, 64 periods of the modulation waveform. The filters are sampled twice every such interval (that is, typically, once every 32 modulation periods) resulting in a set of samples, each of which contains measurements of amplitude and phase of the EEG components present in very narrow frequency bands centered on the modulation frequency and its second harmonic. The phase measurements are made relative to the modulation frequency envelope.

The sets of samples are analysed to provide mean amplitudes, mean phases and probabilities that the distributions of the angles of the samples could have occurred by chance (i.e. in the absence of a phase-locked response). The said probabilities enable the system to decide in real-time whether a response is present. As the system is able to vary both the loudness and the carrier frequency of the auditory signal presented to the patient, it allows objective testing of hearing, which may be performed automatically.

BRIEF DESCRIPTION OF THE DRAWINGS

One preferred embodiment of the invention will now be described with reference to the accompanying drawings in which:

FIG. 6 is a timing diagram showing the ADC timing for sampling of the Hanning filters;

FIG. 10 shows average response amplitudes versus modulation frequency for awake adult subjects with amplitude modulated stimuli at various carrier frequencies (55 dBHL binaural);

FIG. 11 shows average response amplitudes versus modulation frequency for awake and asleep adult subjects with amplitude modulated stimuli at 4 kHz carrier frequency (30 dBSL binaural);

FIG. 12 shows narrow-band background EEG noise as a function of modulation frequency for awake and sleeping adult subjects;

FIG. 14 shows the detection efficiency function of the method at various carrier frequencies for awake and sleeping subjects for 30 dBSL binaural stimulation as a function of modulation frequency.

Referring to FIG. 1 of the drawings, the presently preferred prototype audiometer configuration is shown schematically. The audiometer is controlled by any suitable microcomputer, such as an IBM XT-type, while the EEG signals taken from the patient are amplified by a suitable amplifier, such as a Madsen BPA 77. Selection of carrier frequency and modulation frequency (from the computer keyboard or automatically under program control) sets the frequency of clock oscillators in the "Function Generator" section. These clock oscillators control the frequencies of numerous tracking filters (switched capacitor and other) in both the "Function Cenerator" and "Detector" sections The non-switched capacitor filters are all similar 12 dB per octave low-pass filters which perform such tasks as anti-aliasing as described further below. The computer can also vary the loudness of the stimulus to each ear separately over a range of approximately −10 to 120 dBHL. This is made possible by the "Range Setter" section which attenuates the output to the headphones in increments of 40 dB. Such high sound levels allow the use of the system in measuring the hearing of profoundly deaf infants and children. Protection against accidental overly loud stimuli is threefold: software level limitation, preset hardware cutout and disablement of the highest 40 dB of the system. The output of the function generator drives two buffer amplifiers which drive the headphones (or other transducers such as Etymotic Research Tubephones).

The EEC resulting from the stimulus is picked up using silver-silver chloride (or gold) electrodes on the scalp, is amplified by the EEG amplifier, which is a high impedance, high gain, low noise preamplifier. As described further below, the output of the preamplifier passes through an anti-alias filter and preliminary bandpass filters (one each for the modulation frequency and its second harmonic). The signal (in two channels for the two harmonics) is further amplified and multiplied by the sine and cosine components of the two harmonics. The resulting four channels pass through four anti-alias filters, followed by four low-pass filters. A wide variety of low-pass filters would suffice for this role but here four-pole filters are employed, giving rise to an effective time "window" which approximates the shape of a Hanning window. The duration of the "window" is, typically, 64 modulation periods. Typically, a sampling pulse is generated every 32 cycles of the modulation waveform, resulting in optimum sample overlap so as to have the maximum inter-sample time while maintaining 100% sampling efficiency. The outputs of the low-pass filters provide Fourier analysis of the EEG at the modulation frequency and its second harmonic, both in-phase (cosine) and 90°-shifted (sine) terms. The detection of a response would usually require the collection of from 20 to 256 samples.

The computer analyses the samples (which contain amplitude and phase information at the two frequencies) to obtain the mean amplitudes and mean phases as well as probabilities that the sample distributions might have arisen by chance (i.e. in the absence of a phase-locked response). This processing is done in real-time and the computer stops sampling as soon as the required statistical criteria for the presence of a response have been satisfied.

Figure 1:
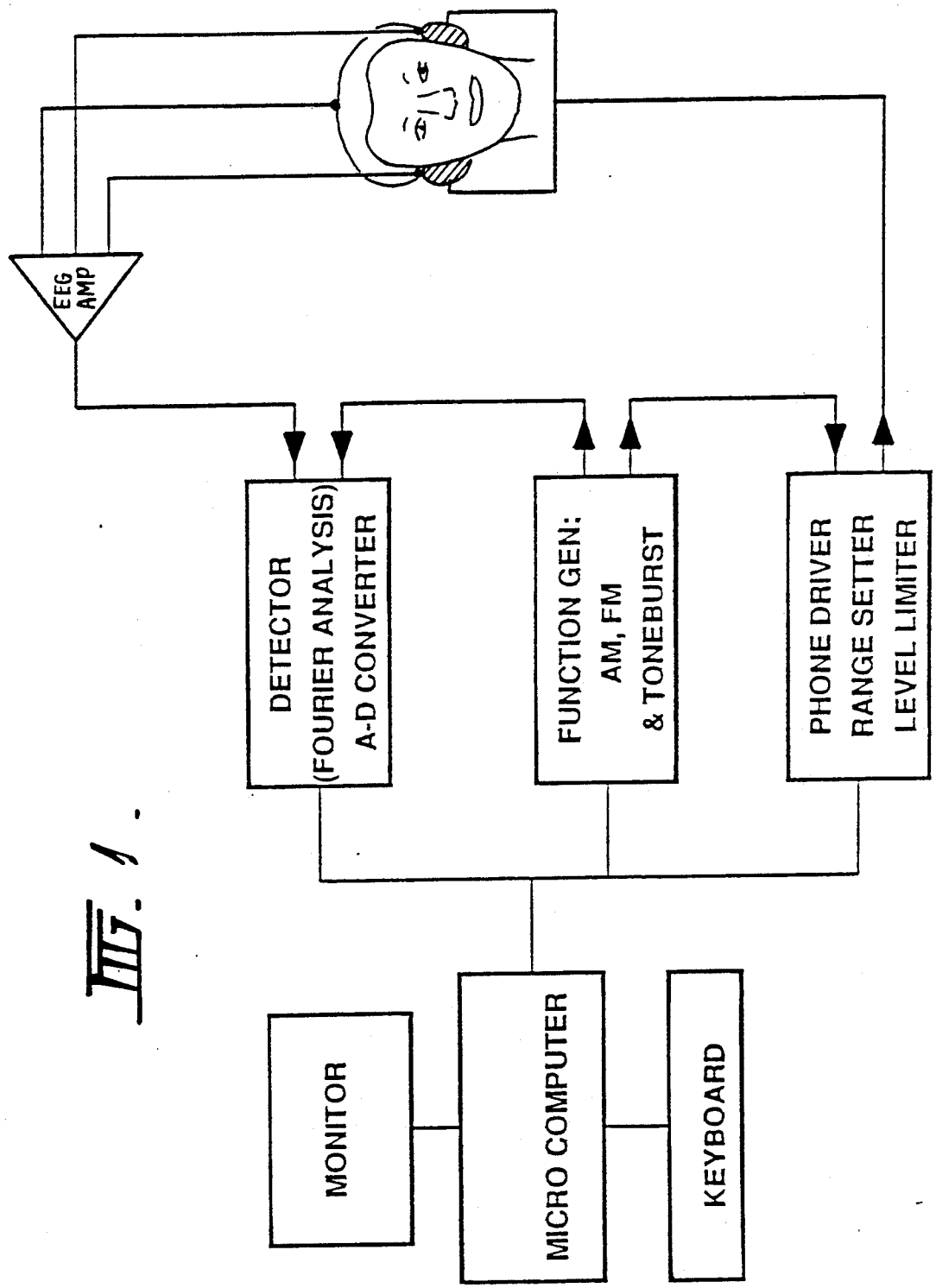
FIG. 1 is a schematic diagram of a preferred audiometer embodying the invention.
Figure 2A:
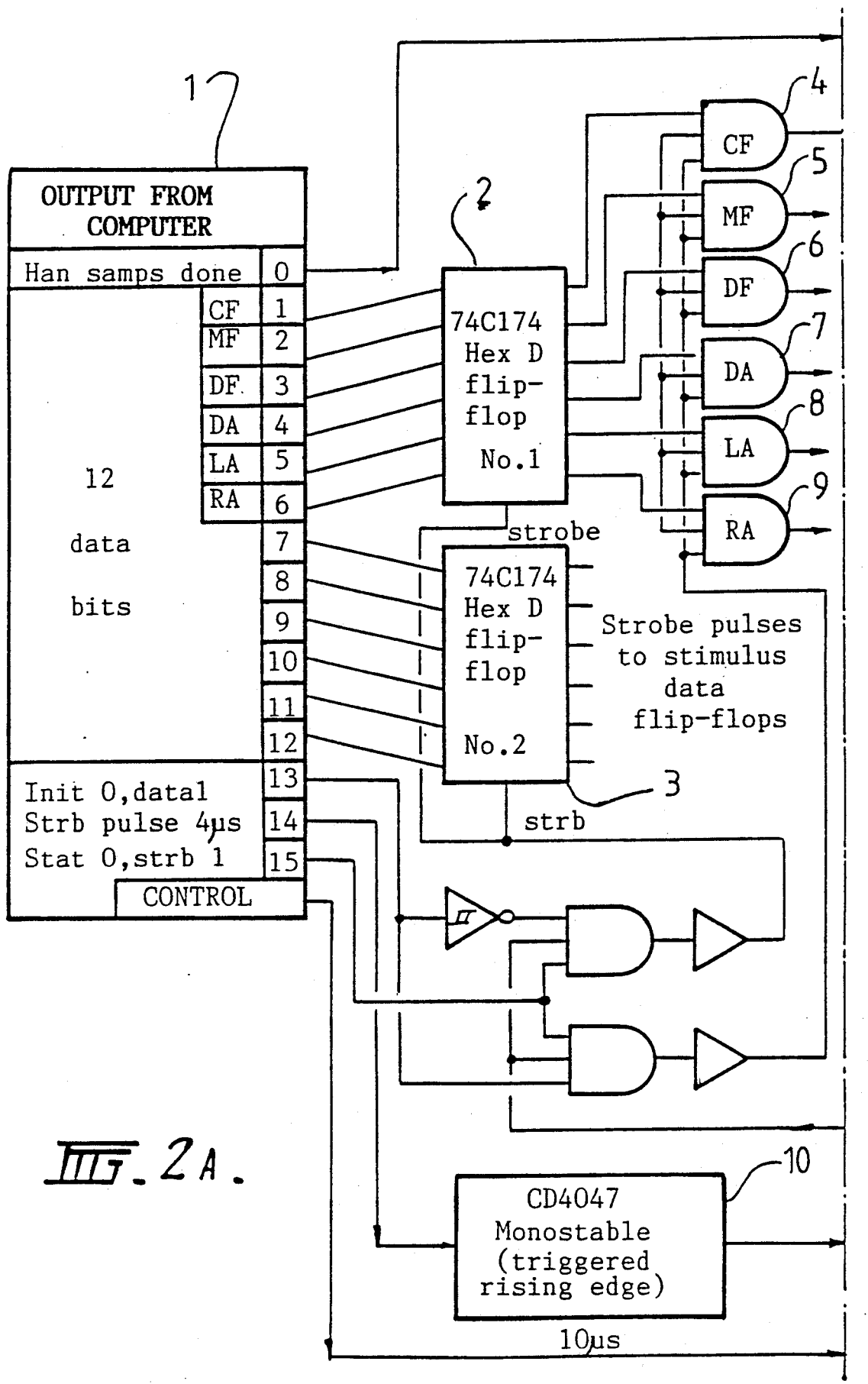
FIG. 2 is a more detailed block diagram of part of the audiometer of FIG. 1 showing the manner in which most stimulus data transmission from computer to audiometer is effected ('strobed' data transmission)
Figure 2C:
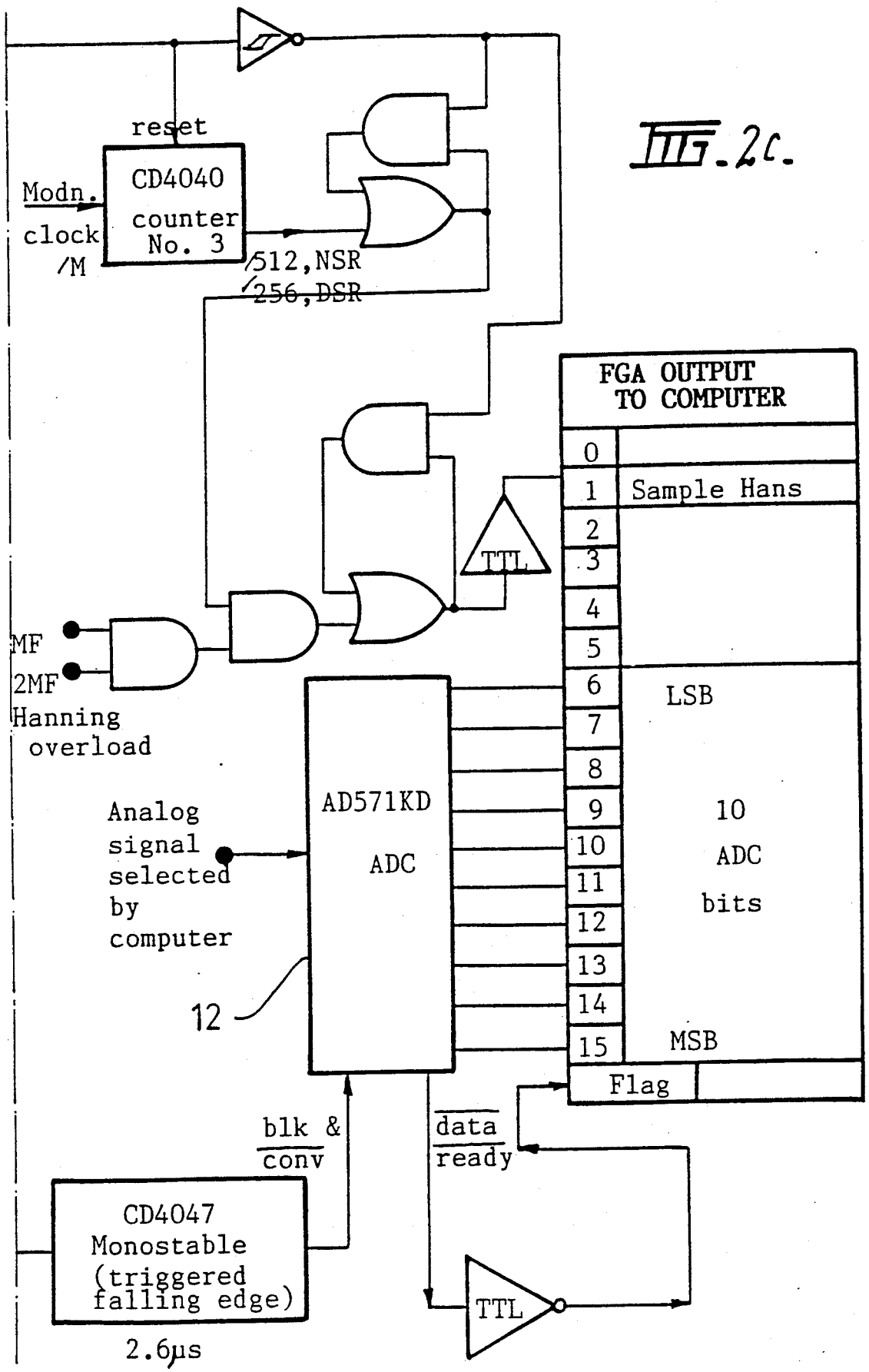

Referring now to FIGS. 2 to 9 of the drawings, which show the essential elements of the audiometer of FIG. 1 in greater detail, data determining carrier frequency (CF), modulation frequency (MF), frequency modulation depth (DF), amplitude modulation depth (DA), stimulus intensity to left ear (LA) and intensity to right ear (RA), represented in FIG. 2 as "output from computer" 1, are strobed into pairs of Hex D flip-flops, for example CF1 and CF2, there being twelve bits of information for each of the above parameters. The number appearing in each circuit block refers to a commercially available circuit component. Prior to the transmission of this data, the audiometer circuit must be informed as to which pair of data flip-flops should be strobed, for example CF1 and CF2 (similar pairs of flip-flops (not shown) are provided for the remaining parameters MF, DF, DA, LA and RA), and which channel of the system is to be addressed (in the present prototype system there is only one channel but there is provision for more if desired). This initialising information is strobed into the Hex D flip-flops 2 and 3. For any strobing to have effect, bit 15 must be set. For the initializing strobing into flip-flops 2 and 3, bit 13 must be low. For initialization, the bits selecting CF (bit 1) and No. 1 channel (bit 7) must be set (and no others among bits 1 to 12). Then the computer must strobe bit 14 with a positive-going pulse (duration approximately 4 us). The setting of bit 1 of both flip-flop 2 and flip-flop 3 (in the present example) enables CF data to be strobed into the first channel, the next step.

Once the desired CF data has been put onto bits 1 to 12, and bit 13 has been set, the actual data can be strobed into flip-flops CF1 and CF2 by a second strobing of bit 14. Strobing pulses are directed to the appropriate pairs of data flip-flops by AND gates 4 to 9. The data for MF, DF, DA, LA and RA are transferred similarly to their respective pairs of flip-flops (not shown) and all the data remains latched into the appropriate flip-flops CF1 and CF2 etc. until it is deliberately altered or the power supply turns off. The effective strobing pulse is independent of the duration of the pulse on bit 14, being transformed by a monostable circuit 10 to 10 us duration and slightly delayed in its onset by delay circuit 11.

Figure 5A:
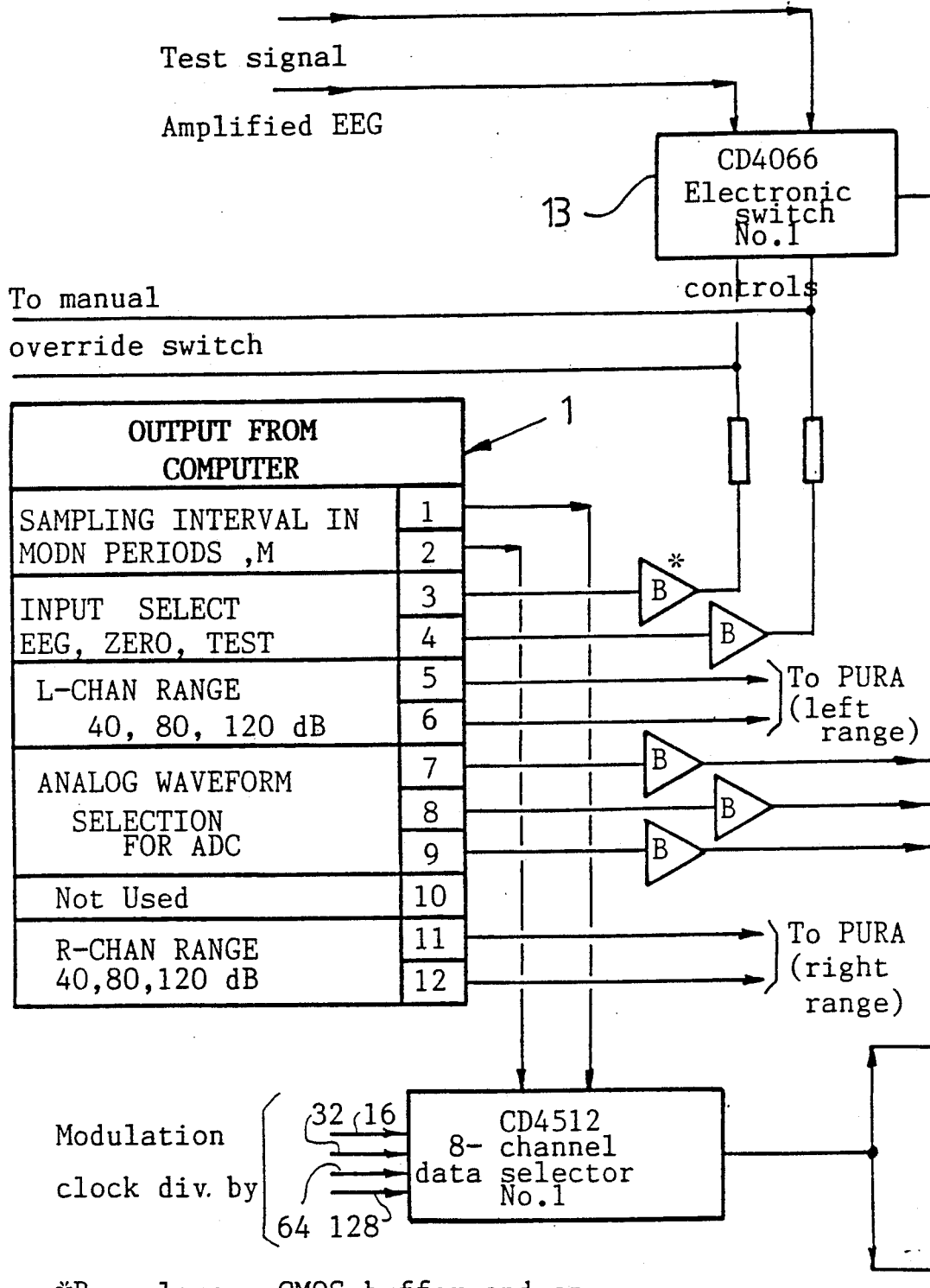
FIG. 5 is a block diagram of a part of the audiometer of FIG. 1 showing the manner in which further data transmission from computer to audiometer is effected ('static' data transmission)
Figure 5B:
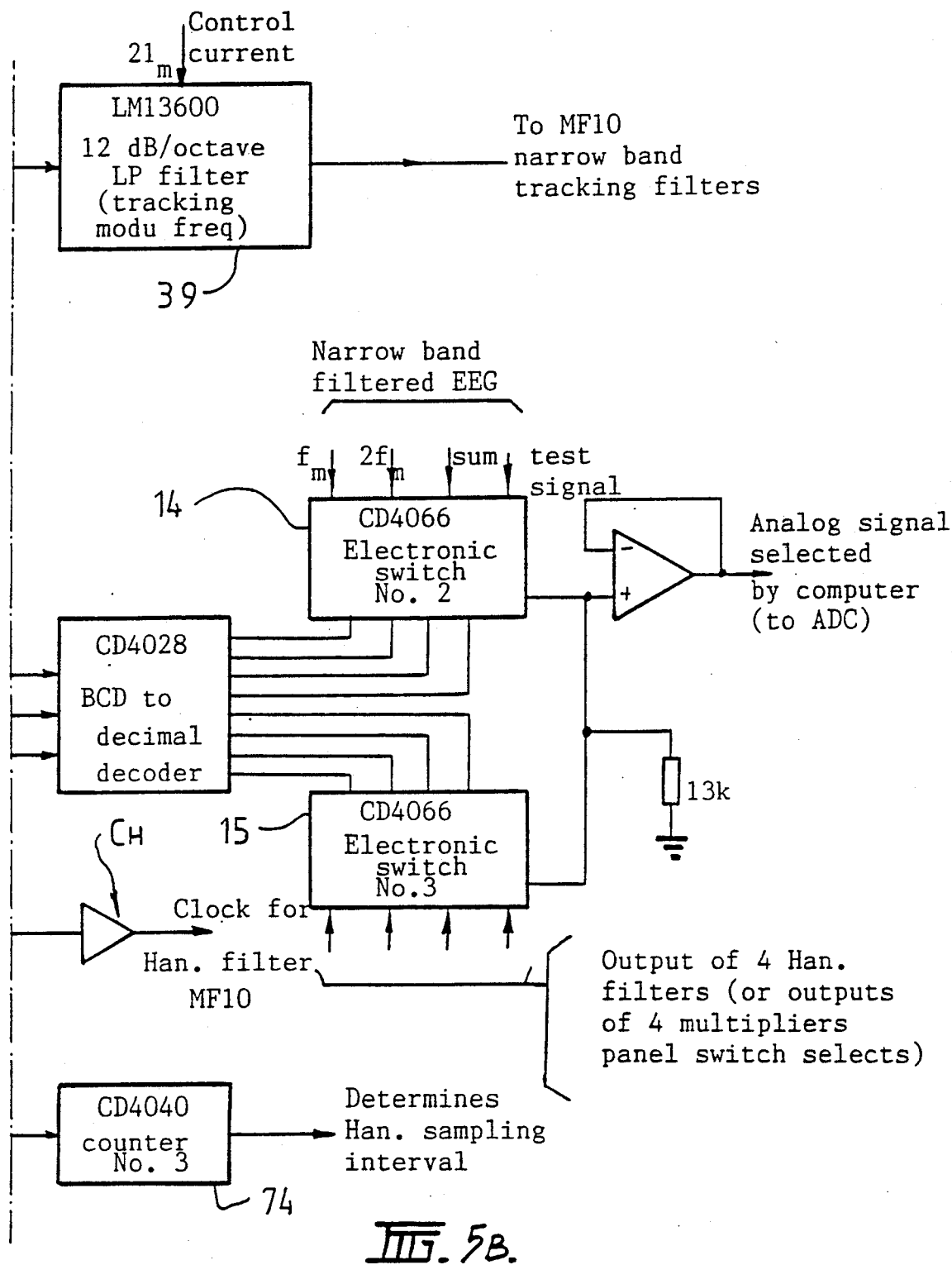

When bit 15 is low, bits 1 to 12 are available to be used for the other, "static", data transmission by means of the circuit detailed in FIG. 5. Bits 1 to 12 then control sampling interval, input selection (EEG, zero or test), left and right ear level ranges and analog waveform selection for input to an analog-to-digital converter (ADC) 12, and must be held at their appropriate values by the computer. Simple RC circuits (not shown) ensure that at appropriate points in the circuitry, the values cannot change during the brief duration of strobing operations. A programmable variable range amplifier (PVRA) circuit (not shown) associated with left and right level ranges (bits 5,6 and 11,12) allows the activation of relays within that circuit to give different degrees of attenuation (0, 40 or 80 dB) to the output signals which will drive the left and right headphones. These level ranges allow a stimulus dynamic range of 130 dB, from 0 to 130 dBSPL.

Figure 3A:
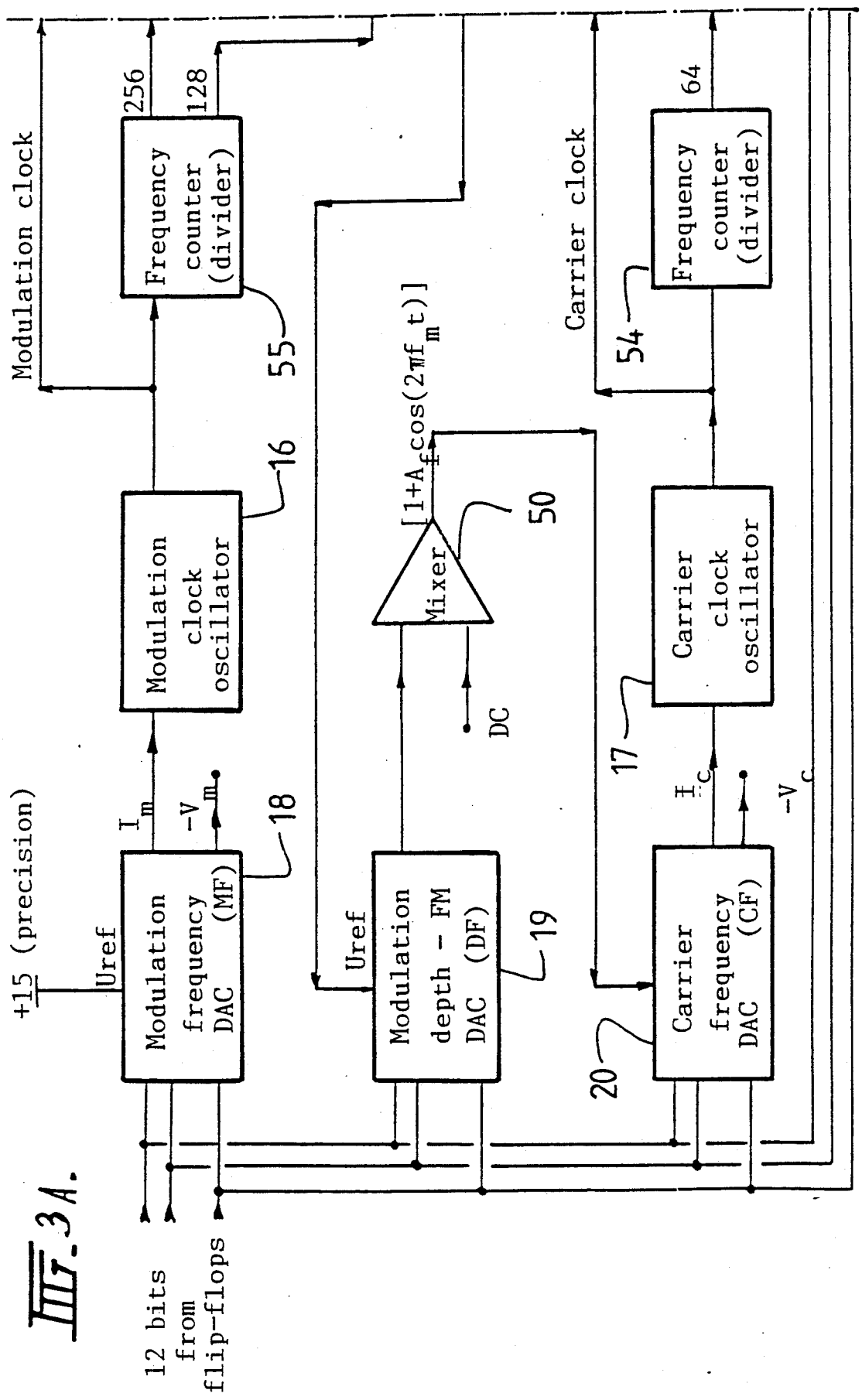
FIG. 3 is a block diagram of the stimulus generation portion of the audiometer.

Bits 3 and 4 allow selection, via an electronic switch 13, of analog input signal: EEG, zero or a test signal. Bits 7,8 and 9 allow selection, via two electronic switches 14 and 15, of any one of eight possible analog outputs to the ADC 12. These outputs include the outputs of final "Hanning" filters, yet to be described Selection of carrier frequency and modulation frequency (from the computer keyboard or automatically under program control) sets the frequency of clock oscillators 17 and 16 in the stimulus generation section of the audiometer, as shown in FIG. 3. The outputs of the relevant flip-flops CF1, CF2 etc. provide digital inputs to multiplying digital-to-analog converters (DAC) 20 cd and 18, (as well as 19, 35, 36 and 37), the outputs of which are the products of their digital and analog inputs. The main outputs produced are currents, Ic and Im, which control the frequencies of two current controlled oscillator circuits 17 and 16. The square wave outputs of the oscillators 17 and 16 (approximately −14 to +14 V) are modified by known signal shaping means (not shown) to give final square wave clock waveforms of 0 to +5 V.

Voltages −Vin(c) and −Vin(m) proportional to Ic and Im, are also generated and are used as inputs to voltage-to-current conversion circuits (not shown), whose outputs are proportional to Ic and Im, respectively. The currents are then used to control the operating frequencies of numerous "scavenging" low pass filters, as described further below, used to perform such tasks as anti-aliasing and removal of clock noise from the outputs of switched-capacitor filters.

Figure 4A:
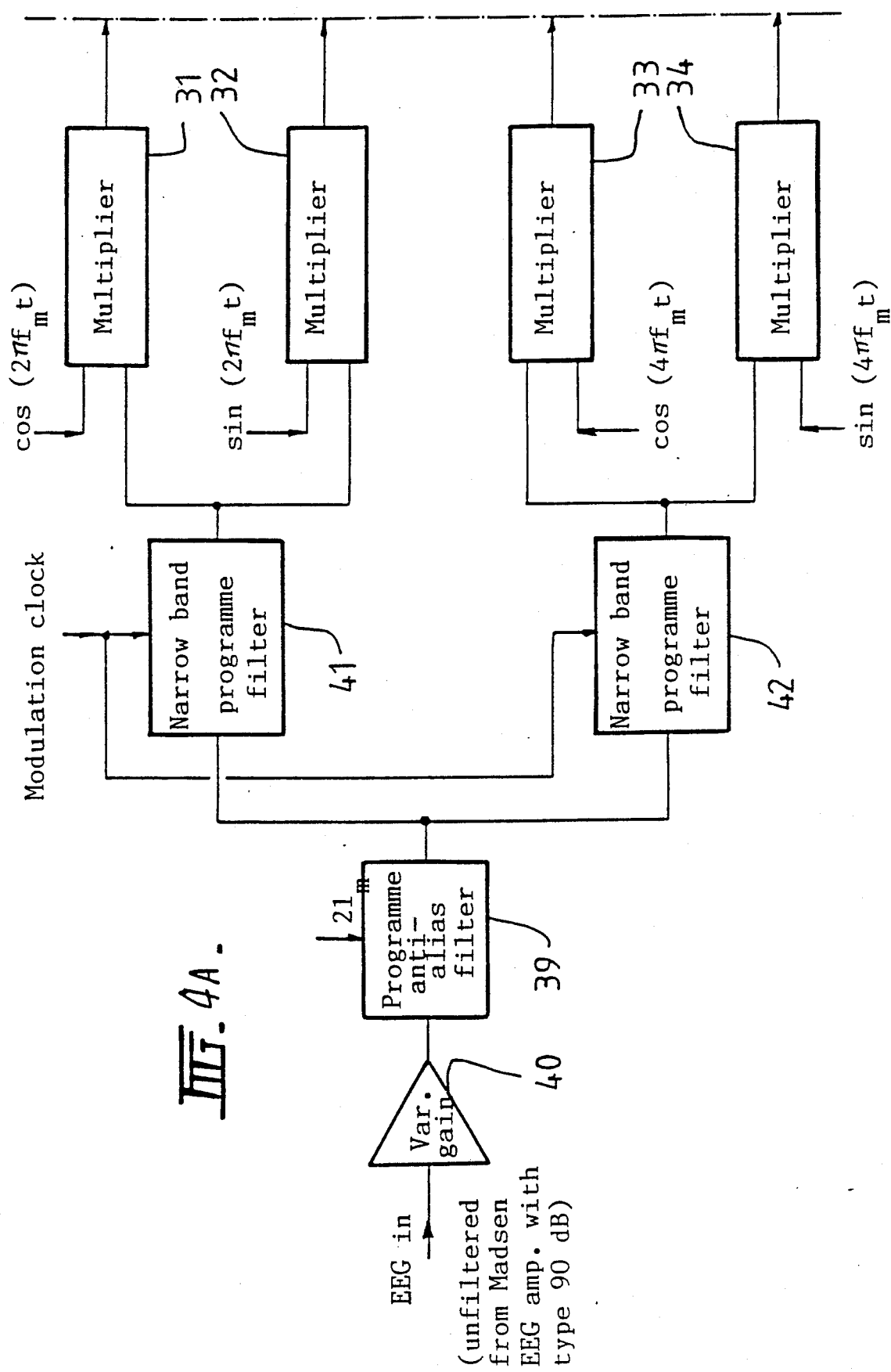
FIG. 4 is a block diagram of the signal detection portion of the audiometer.
Figure 7A:
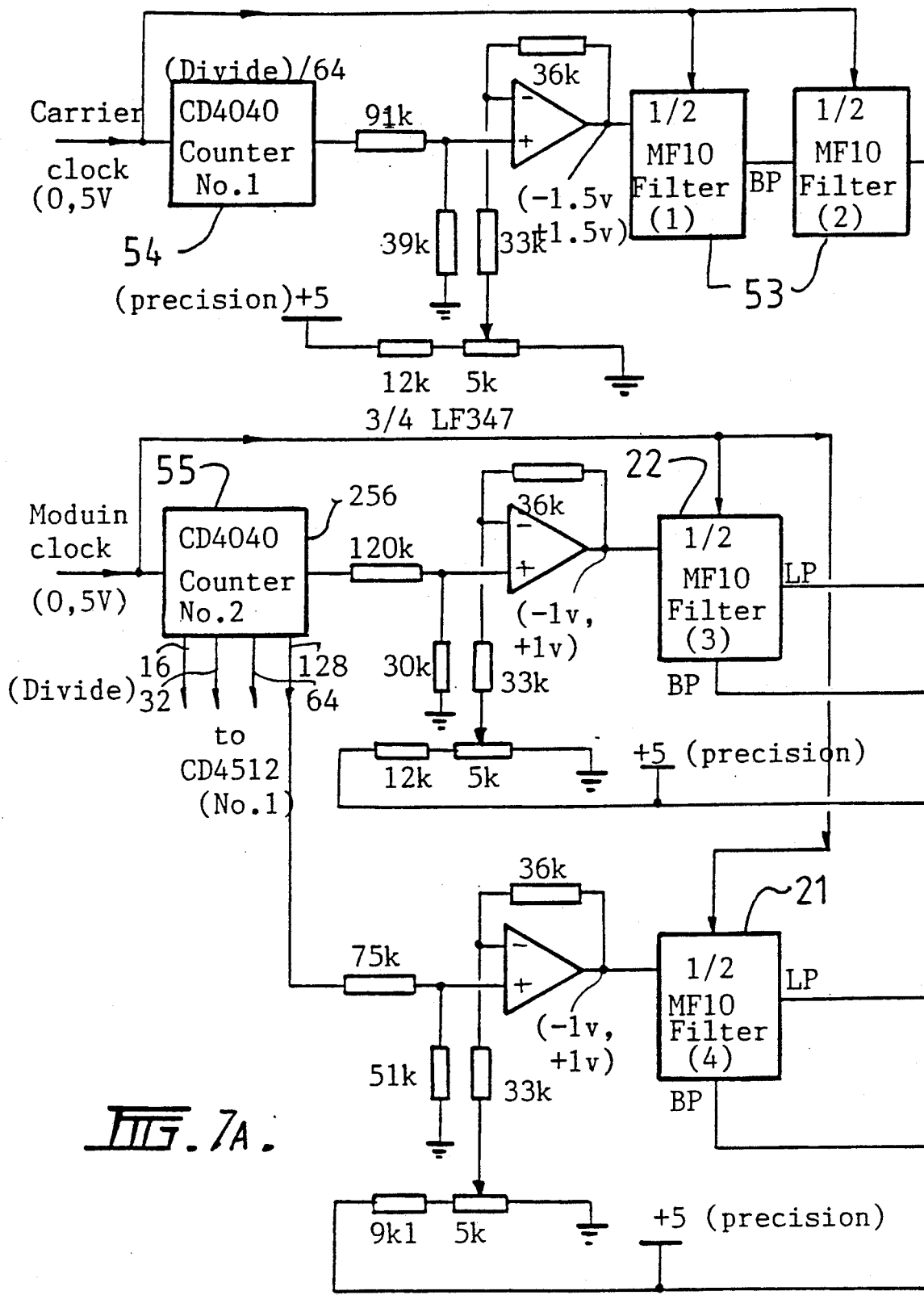
FIG. 7 is a more detailed block diagram showing the circuit for generating the carrier, modulation sine waves and quadrature components of the stimulus signal.
Figure 7B:
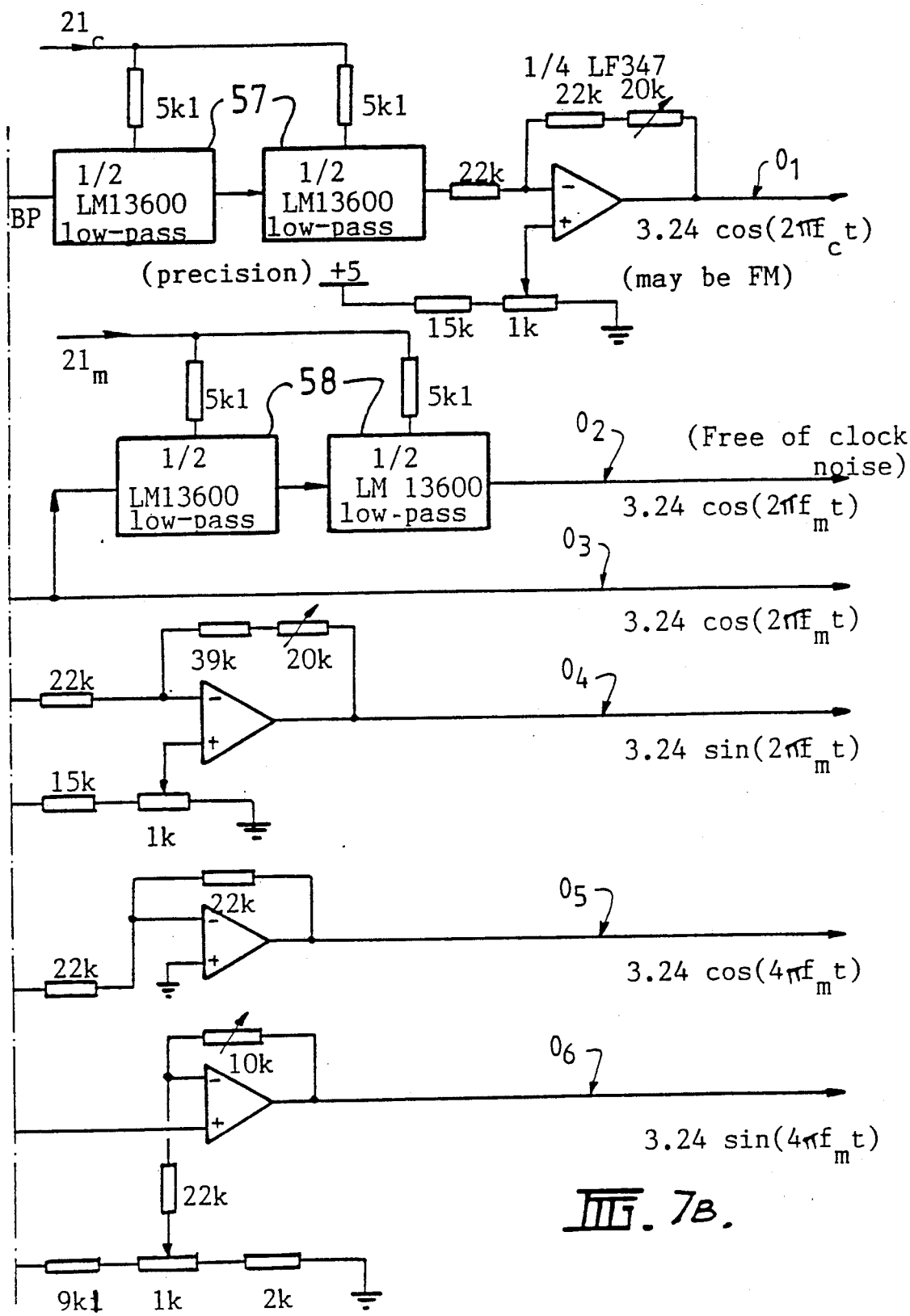
Figure 9B:
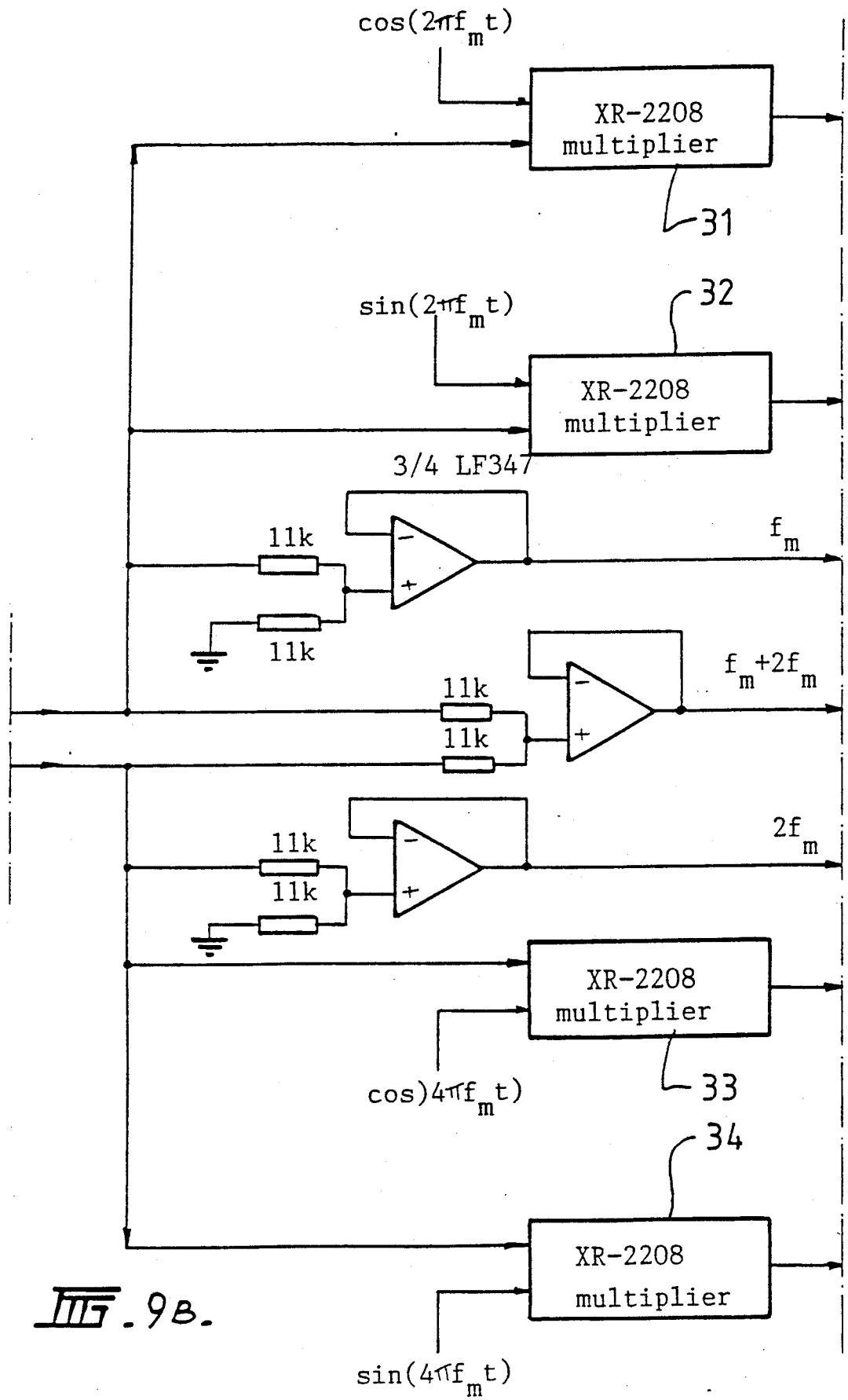
FIG. 9 is a more detailed block diagram showing the signal detection circuitry.
Figure 9C:
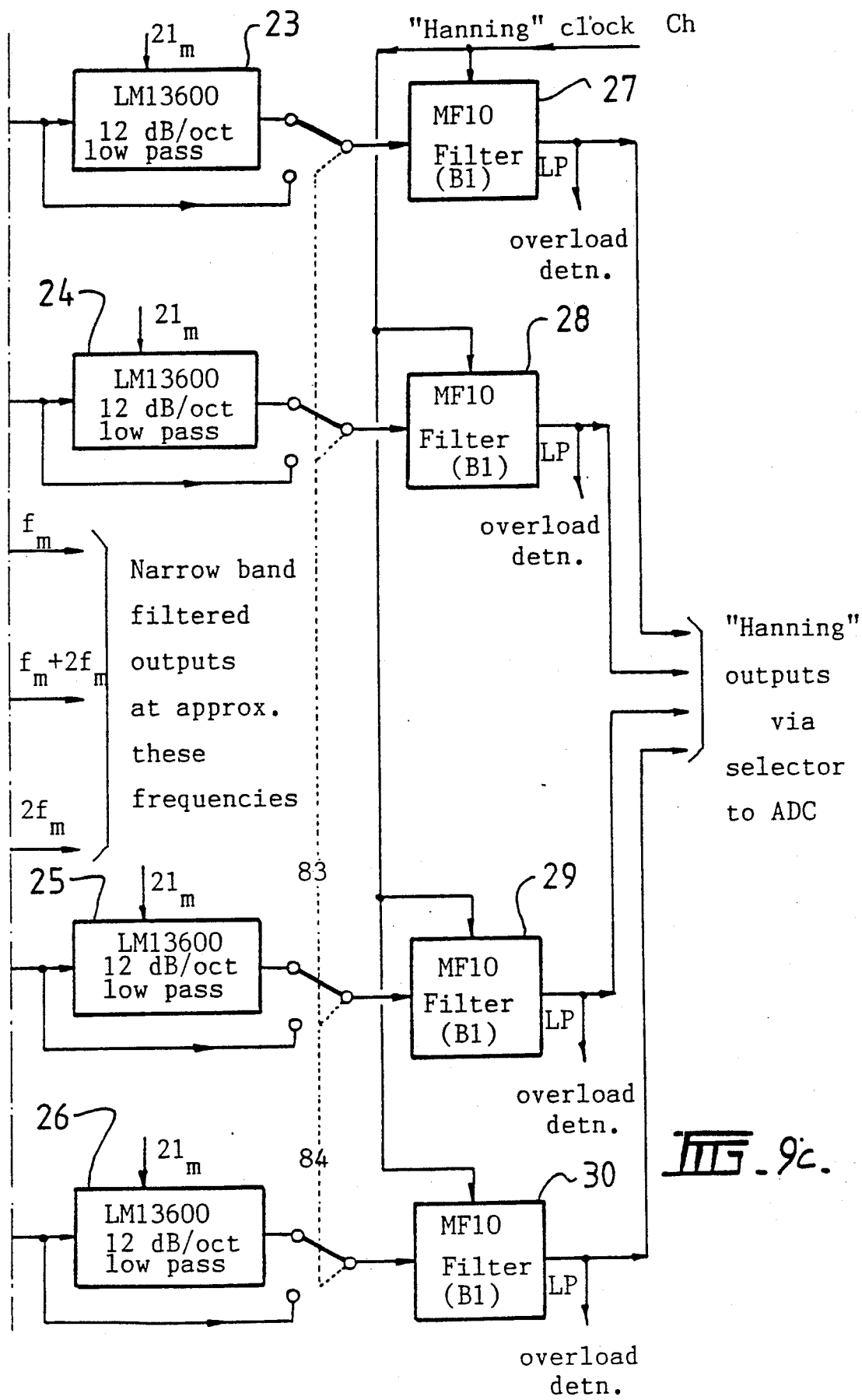

The clock oscillators 17 and 16 control the frequencies of numerous tracking filters, both switched capacitor and "scavenging" in the stimulus generation circuit of FIGS. 3 and 7 and the signal detection circuit of FIG. 4. The square wave clock output of oscillator 17 (16) is divided in frequency by 64 (256 and 128) by frequency counter or divider circuits 54 and 55 to provide the actual carrier frequency CF (modulation frequency MF and its second harmonic), which are passed through switched capacitor filters 53, 21 and 22 to become sinusoidal and, in the case of the modulation frequency, to generate quadrature cosine and sine components (see FIGS. 3 and 7). The quadrature output components are simply taken from the lowpass (LP) and bandpass (BP) outputs of the switched capacitor filters 21 and 22 (FIG. 7). The sinusoidal outputs $O_1$ and $O_2$ from the stimulus generation circuit, as best shown in FIG. 7, provide the actual carrier and modulation waveforms and these have had residual clock noise filtered out by low pass filters 57 and 58. The remaining outputs $O_3$ to $O_6$ provide inputs for signal detection multipliers 31 to 34 inputting to anti-aliasing filters 23 to 26 (FIGS. 4 and 9). It is not necessary to remove clock noise from these outputs.

Figure 8B:
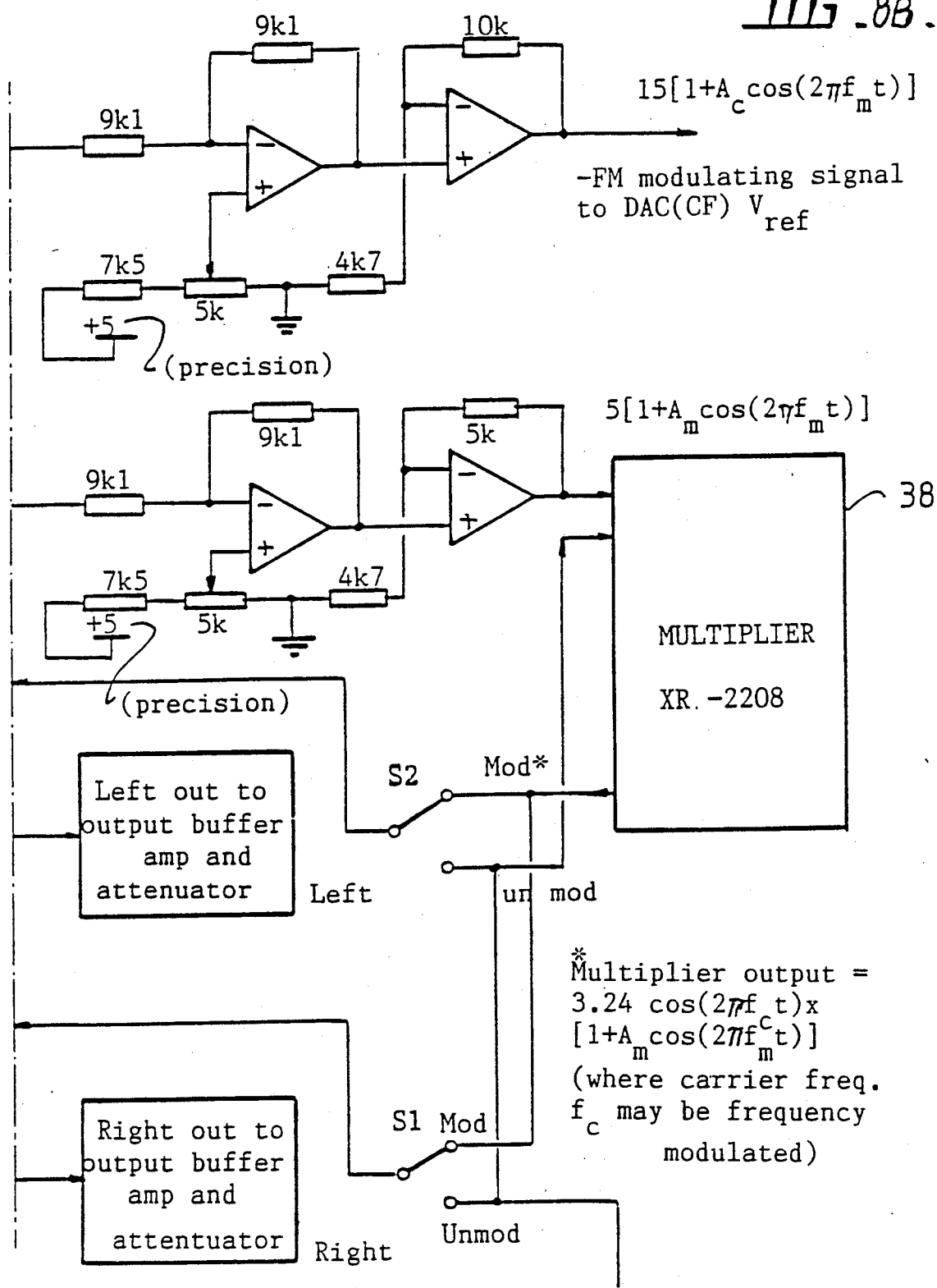
FIG. 8 is a more detailed block diagram showing the circuit for controlling the modulation and level of the stimulus signals.

Amplitude modulation of the stimulus signal, of variable modulation depth, is possible using analog multiplication of the carrier by a constant plus a term proportional to the modulation waveform (FIG. 3 and FIG. 8). The amplitude modulation depth is proportional to the digital input to a multiplying DAC 35. A similar frequency modulating signal (constant plus a term proportional to the modulation waveform) is generated, with the frequency modulation depth determined by the digital input to the multiplying DAC 19. This signal is taken to the analog input of the multiplying DAC 20 via a mixer, resulting in a modulated current input to the current controlled oscillation 17, the output of which is frequency modulated The sound levels to the two ears are controlled by the two multiplying DACs 36 and 37, best seen in FIG. 8 The carrier signal, which may already be frequency modulated, is multiplied by the amplitude modulation signal from 35 using multiplier 38. Switch means $S_1$ and $S_2$ (FIG. 8) allow the amplitude modulation to be switched on or off separately for the two ears, enabling binaural stimuli, with one ear modulated and one not.

The stimulus signals are buffered by a unity gain circuit (not shown), which is able to drive the earphones to levels of up to 130 dBSPL, in the case of TDH-39 earphones. The computer controlled relays in the PVEA circuitry (not shown) allow attenuation of 0 dB, 40 dB or 80 dB. Accordingly, output levels are available from about 0 dBSPL to 130 dBSPL, as the level control DACs 36 and 37 easily allow control over a range of 50 dB. The availability of such high sound levels allows the use of the system in measuring the hearing of profoundly deaf infants and children. Protection against accidental overly loud stimuli is threefold: software level limitation, preset hardware cutout and disablement of the highest 40 dB of the system, each performed in a known manner not shown in the drawings.

Similarly, tonebursts or more general modulated waveforms may be generated by multiplication of the carrier waveform by the output of a simple periodic envelope generator circuit (not shown, but preferably with linear ramp waveforms at onset and offset of each burst and a plateau region) or, more generally, by a modulation waveform stored in a random access memory (RAM), for example, a UM6116 device. The rate at which the RAM waveform is read is governed by the previously mentioned modulation clock frequency. The RAM circuitry is similarly not shown.

Good combinations of large response amplitude and frequency specificity can be obtained using two stimulus types. One is a band-limited toneburst, the envelope of which is calculated and stored in a RAM (not shown). The resultant toneburst retains the five central harmonics of a normal tone burst, and also retains a fairly rapid onset/offset and a substantial quiescent period during each modulation cycle. The other is a combination of amplitude and frequency modulations, which gives more "character" to the "onset" of the waveform (relative to AM) and gives a combination of the good performance of AM at high carrier frequencies and the good performance of FM at low carrier frequencies.

The frequency specificity of any stimulus can be enhanced by the use of high-pass filtered masking noise to ensure that a high frequency region of the basilar membrane is not spuriously excited.

Referring to FIGS. 4 and 9, the output from the EEG amplifier (FIG. 1) is passed through a programmable anti-alias filter 39 via a variable gain amplifier 40 and then through two preliminary band-pass (switched capacitor) filters 41 and 42 (one each for the modulation frequency and its second harmonic). The two signal channels (for the two harmonics) then pass through further amplifiers 43,44 (FIG. 9) and are multiplied by the sine and cosine components of the two harmonics by means of the multipliers 31 to 34. The resulting four signal channels pass through the four anti-alias filters 23 to 26, followed by the four low-pass switched capacitor filters 27 to 30. The operating frequencies of these last "Hanning" filters are determined by their clock inputs CH (FIG. 9), which are equal to the modulation clock frequency divided by 16, 32, 64 or 128, for sample lengths of 16, 32, 64 or 128 modulation periods, as shown in FIG. 5. The "Hanning" clock frequency is further divided by 256 by divider circuit 74 (FIG. 5) to obtain pulses for instructing the computer to initiate sampling of the "Hanning" filter outputs.

A wide range of low-pass filter shapes would suffice for this role, including a single pole low-pass filter, but here four pole filters are employed (each comprising four cascaded identical single pole filters), giving rise to an effective sampling time "window" which approximates a Hanning window, namely $[1-\cos(2\pi t/t_H)]/2$, where $t_H$ is the width of the window, or sample length (and the function is only defined for $0 \leq t < t_H$). The width of the "window" is, typically, approximately 64 modulation periods. Typically, a sampling pulse is generated every 32 cycles of the modulation waveform, resulting in some degree of sample overlap. For a given inter-sample interval, ts, there is an optimum value of $t_H$ such that there is essentially 100% efficiency in the data collection, but minimum overlap of samples. Cf there are large gaps between the samples, clearly much information will be lost, but if the samples overlap substantially, the information contained in a given sample will not be independent from that contained in adjoining samples.

For the window shape in question, the optimum value of $t_H$ is approximately 2ts. If a single pole low-pass filter had been used, if ts had remained the same and 100% efficiency had been required, the amount of sample overlap would have been considerably greater. Viewed another way, if both single pole filters and 4 pole filters were arranged to have 5% sample overlaps, the sampling efficiencies would be 60% and approximately 80%, respectively. Bits 7, 8 and 9 from the computer control the selection of the four filter outputs in turn. The computer then controls the sampling of each filter output by the analogue to digital converter (ADC) 12 (FIG. 4) under the control of an output selector 46. A timing diagram for the ADC sampling is shown in FIG. 6.

The outputs of the low-pass filters 27 to 30 provide Fourier analysis of the EEG at the modulation frequency and its second harmonic, both in-phase (cosine) and 90°-shifted (sine) terms. The computer analyses the samples (which contain amplitude and phase information at the two frequencies) to obtain the mean amplitudes and mean phases It also calculates probabilities that the sample distributions might have arisen by chance (i.e., in the absence of a phase-locked response). This provides a quantitative measure of the likelihood of a hearing response being present. A function F(N) is defined such that:

$$F(N) = \left\{ (2/N) \left[ \sum_{i=1}^{N} \cos \theta_i \right]^2 + \left[ \sum_{i=1}^{N} \sin \theta_i \right]^2 \right\}$$

where N is the number of samples and $\theta_i$ are the individual sample angles. This function follows a Chi-squared distribution with two degrees of freedom. The computer can readily calculate the probability, using the function $P\% = 100 \exp(-0.5027F)$, a good approximation to the Chi-squared distribution, that the given distribution of angles could have arisen from random noise background, in absence of a response. If F(N) is large, the probability of the angle distribution having arisen from random noise is very small and the presence of a response is very likely.

In the case of moderate sample overlap, the statistics are distorted and a value Q, less than 1.0, can be found such that $$F(N) = \left\{ Q \times (2/N) \left[ \sum_{i=1}^{N} \cos \theta_i \right]^2 + \left[ \sum_{i=1}^{N} \sin \theta_i \right]^2 \right\}$$

also follows a Chi-squared distribution. If samples are required not to overlap, as when $t_H = ts$, the sampling efficiency is about 80%, which means that detection of a response takes (1/0.8) times as long.

This statistical processing is done in real-time between samplings of the output filters 27 to 30 and the computer stops sampling as soon as the required statistical criteria for the presence of a response have been satisfied.

The statistics to this point accurately describe the distribution of probability P (derived from F(N)) that one would obtain from say 100 runs in the absence of a response, each run being sampled just once during its data collection. For example, we would find, on average, that only 1 run would have $P \leq 1\%$. However, because we wish to identify the presence of a response as soon as possible during a run, we measure P continually, not just once during a run. This distorts the statistics and, indeed, the probability of a run having $P \leq 1\%$ at some stage of its data collection may be as high as 10% if the total number of sample points in a run is 256.

Numerous approaches to this problem could be taken, each with rather similar results. The approach taken in the present form of the invention was to require $P \leq 1\%$ for 0.07 N or 2 sample points, whichever is larger. Hence, the more points which have been collected, the longer P must be $\leq 1\%$. This gives a false hit rate of about 5% after 256 sample points. In addition, depending on the circumstances, including the size of response expected, a response may not be allowed before a certain number of points have elapsed. This number has been 64 with infants. This further reduces the percentage of false hits by 1 or 2%.

A hearing threshold may be estimated by varying the loudness of the stimulus in, say, 10 dB increments until the softest sound is found that elicits a response. Alternatively several measurements may be made above threshold and the intercept of amplitude vs. level graph may be estimated. The detection of a response would usually require the collection of from 20 to 256 samples.

FIG. 10 shows average response amplitudes (at the modulation frequency) vs. modulation frequency for five carrier frequencies in awake adults in response to amplitude modulated stimuli at 55 dBHL, binaural. There is a strong peak at 40 Hz modulation frequency for all CFs, followed by a minimum at 60–70 Hz and reduced activity above 70 Hz. These results are representative of what is found with a wide variety of modulated tones, for example, tone bursts. Even pure FM gives quite similar results, especially at low carrier frequencies.

FIG. 11 shows a similar curve for awake adult subjects at 4 kHz, 30 dBSL biaaural AM. Again there is the 40 Hz peak followed by diminished activity, not much above the noise floor of the measuring system (not shown). Also shown in this Figure is a comparable curve for sleeping adult subjects. The 40 Hz region, represented by the circle, is dramatically reduced compared to the waking state. The amplitude at higher modulation rates is also reduced but not nearly as much as in the 40 Hz region.

Figure 13:
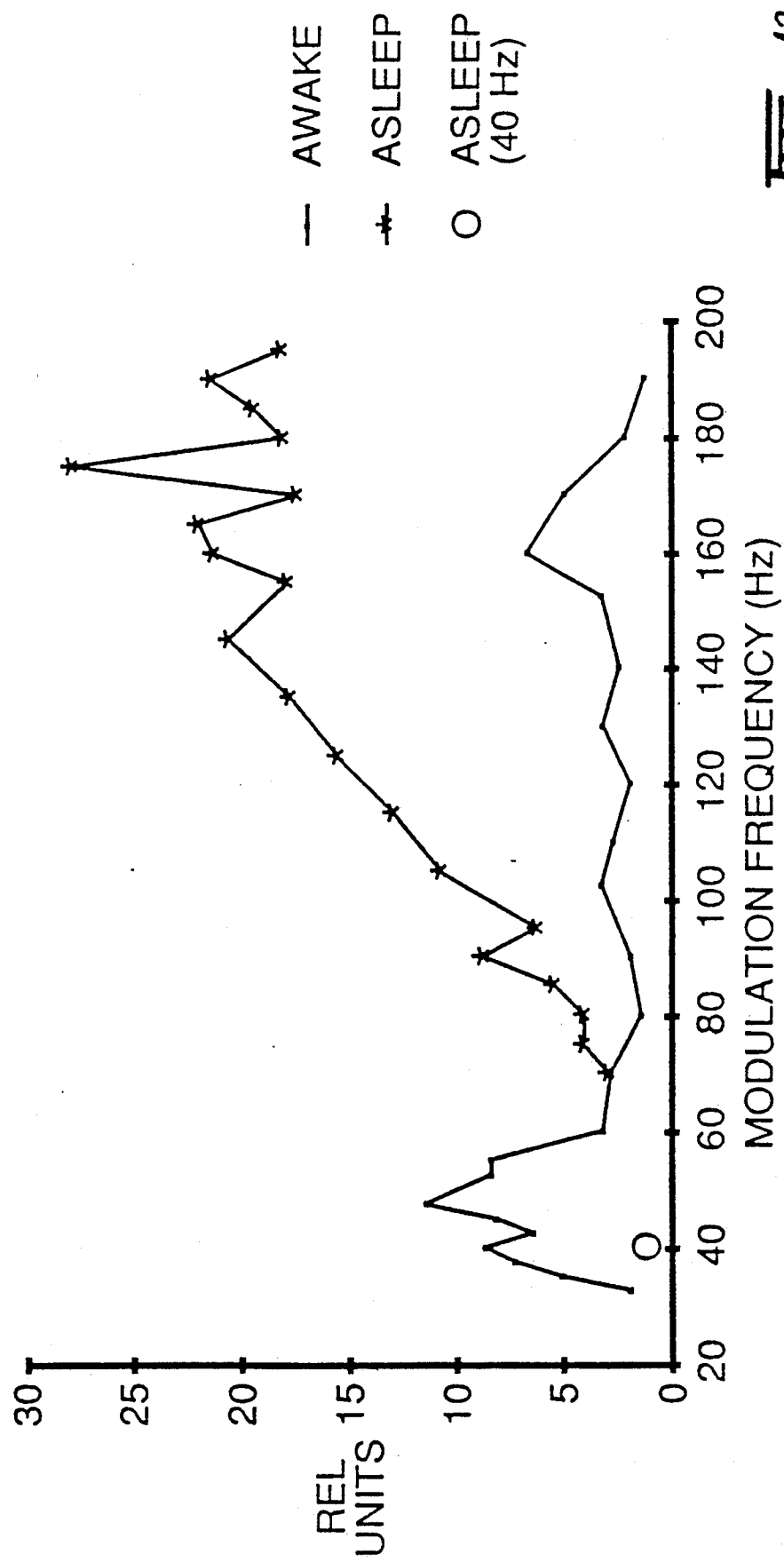
FIG. 13 shows a detection efficiency function for 30 dBSL binaural stimulation at 4 kHz in awake and sleeping subjects, as a function of modulation frequency.

The "detectability" of a response depends primarily on amplitude and noise, in this case the amount of random background EEG noise that is detected by the very narrow band filters implicit in the Fourier analysis. FIG. 12 plots the noise as a function of modulation frequency for awake and sleeping subjects. In sleep the noise is reduced at all frequencies shown, but dramatically so at higher frequencies. Accordingly, the signal-to-noise ratio actually increases with sleep at higher modulation frequencies. We can calculate a Detection Efficiency Function which is proportional to the reciprocal of the time taken to detect a response. It is given by:

$$(S/N)^2 \times F_m$$

where S is the amplitude of the response, N is the noise level and $F_m$ is the modulation frequency The results at 4 kHz from FIG. 11 give rise to Detection Efficiencies as shown in FIG. 13. Not only are the higher modulation rates during sleep dramatically better than 40 Hz, but we can expect to detect a response during sleep in about half the time it would take with the optimum modulation frequency in the awake state.

Similar curves are shown in FIG. 14 for five CFs with combined AM and FM stimuli (30 dBSL, binaural). 4 kHz benefits most from the higher modulation rates but even at 500 Hz frequencies in the 80-100 Hz region are a little better on average than at 40 Hz. 40 Hz amplitudes are not only small but very variable in sleep. Clearly, different CFs will be best suited by different modulation rates.

Figure 15:
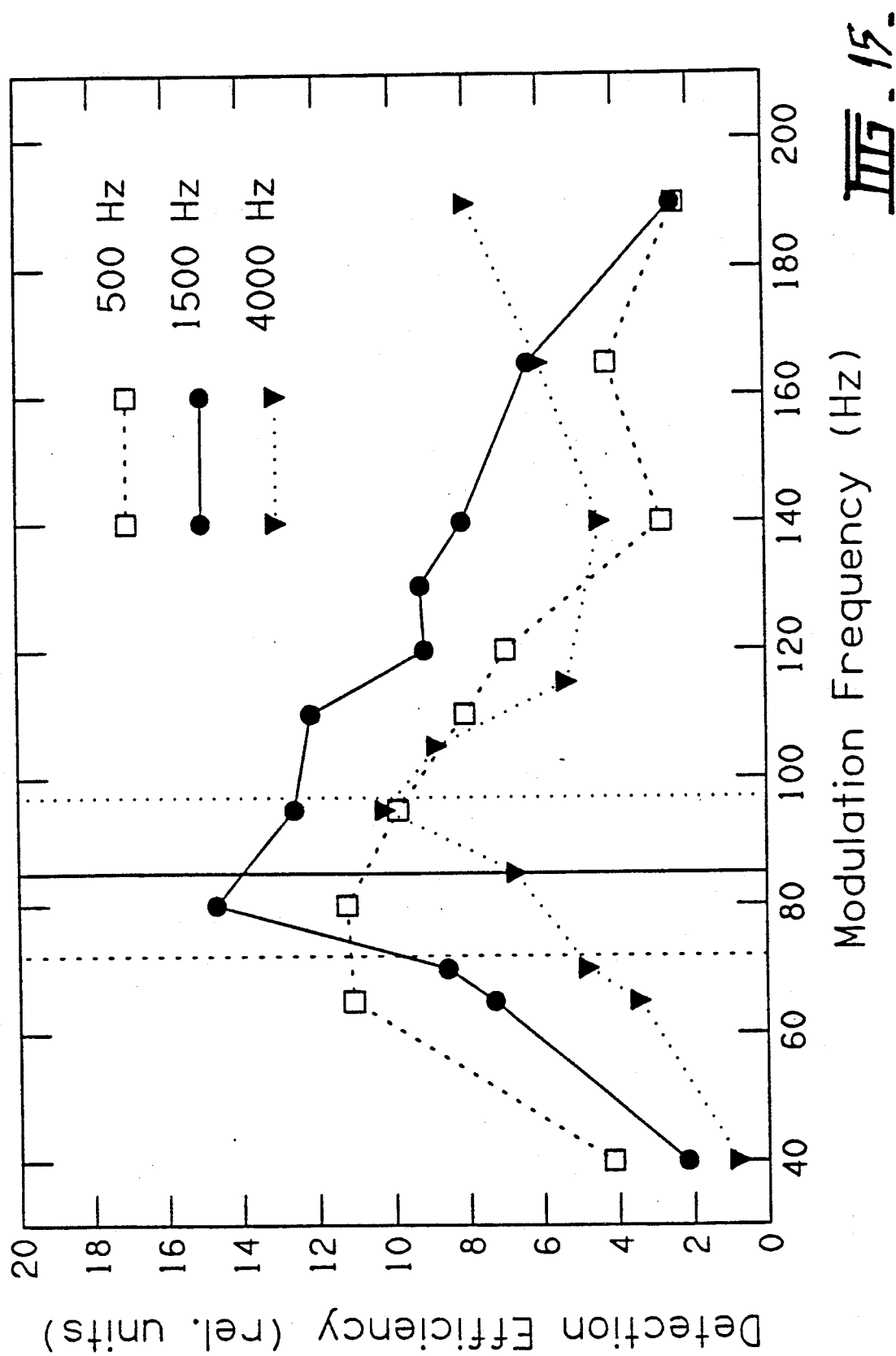
FIG. 15 shows the detection efficiency function of the method at three suitable carrier frequencies for sleeping neonates for 55 dBHL monaural stimulation as a function of modulation frequency.

In FIG. 15 Detection Efficiencies are shown for averages over 10 neonates (less than 1 week old), for monaural stimulation with combined AM and FM stimuli at 55 dBHL at three carrier frequencies. Again, optimum modulation rates are found to be in excess of 60 Hz.

What is claimed is:

1. An evoked response audiometer comprising means of supplying to a sleeping patient an auditory signal consisting of a carrier frequency which is periodically modulated such that the stimulus is at least substantially frequency specific, said auditory signal being presented for a sufficiently extended period of time to enable phase-locked steady-state potentials to be evoked in the brain, means for sampling the brain potential signals evoked by said signal, and means for analysing said brain potentials to determine whether phase-locking of said brain potentials to the modulated auditory signal has occurred, said auditory signal means being controlled so that said auditory signals are periodically modulated at frequencies of at least 70 Hz, the frequency of modulation being varied in a generally increasing manner for auditory signals of higher frequencies.

2. The audiometer of claim 1, wherein said frequency of modulation is about 70-115 Hz for auditory signals having frequencies less than or equal to 1.5 kHz, and said frequency of modulation is about 75-200 Hz (or more) for auditory signals having frequencies in excess of 1.5 kHz.

3. A method of testing the hearing of a sleeping patient comprising the steps of:
supplying to said sleeping patient an auditory signal consisting of a carrier frequency which is periodically modulated at frequencies in excess of 70 Hz such that the stimulus is at least substantially frequency specific, said auditory signal being presented for sufficiently extended period of time to enable phase-locked steady-state potentials to be evoked in the brain,
sampling the brain potential signals evoked by said signal, and
analysing said brain potentials to determine whether phase-locking of said brain potentials to the modulated auditory signal has occurred, the frequency of modulation being varied in a generally increasing manner for auditory signals of higher frequencies.

4. An evoked response audiometer comprising means of supplying to a sleeping patient an auditory signal consisting of a carrier frequency which is periodically modulated such that the stimulus is at least substantially frequency specific, said auditory signal being presented for a sufficiently extended period of time to enable phase-locked steady-state potentials to be evoked in the brain, means for sampling the brain potential signals evoked by said signal, and means for analyzing said brain potentials to determine whether phase-locking of said brain potentials to the modulated auditory signals has occurred, said auditory signal means being controlled so that said auditory signals are periodically modulated at frequencies selected according to the following table:

| Auditory Signal | Modulation Frequency |
| --- | --- |
| (a) Normal Sleeping Neonates | |
| 500 Hz: | at least 70 Hz and substantially within the range of 70-140 Hz, |
| 1.5 kHz: | at least 75 Hz and substantially within the range of 75-165 Hz, |
| 4 kHz: | at least 75 to at least 200 Hz, |
| (b) Normal Sleeping Adults | |
| 250 Hz: | at least 70 Hz and substantially within the range of 75-130 Hz, |
| 500 Hz: | at least 75 Hz and substantially within the range of 75-180 Hz, |
| 1 kHz: | at least 75 Hz and substantially within the range of 75-200 Hz, |
| 2 kHz: | at least 75 to at least 200 Hz, |
| 4 kHz: | at least 75 to at least 200 Hz. |

5. The audiometer of claim 4, wherein, for maturing infants, the modulation frequency for each auditory signal is gradually increased with age towards the modulation frequency specified for adults.

6. The audiometer of claim 4, wherein said auditory signal supplying means is controlled by a computer programmed to select the most appropriate modulation frequency for each stimulus frequency depending on the nature of the patient and their state of arousal.

7. The audiometer of claim 4 wherein said modulation frequencies are selected from:

| Auditory Signal | Modulation Frequency |
| --- | --- |
| (a) Normal Sleeping Neonates | |
| 500 Hz: | substantially within the range of 70-95 Hz, |
| 1.5 kHz: | substantially within the range of 75-115 Hz, |
| 4 kHz: | at least 85 to at least 200 Hz, |
| (b) Normal Sleeping Adults | |
| 250 Hz: | substantially within the range of 80-115 Hz, |
| 500 Hz: | substantially within the range of 80-115 Hz, |
| 1 kHz: | substantially within the range of 80-115 Hz, |
| 2 kHz: | substantially within the range of 85-195 Hz, |
| 4 kHz: | at least 85 to at least 200 Hz. |

8. The audiometer of claim 4 wherein said modulation frequencies are:

| Auditory Signal | Modulation Frequency |
| --- | --- |
| (a) Normal Sleeping Neonates | |
| 500 Hz: | about 72 Hz, |
| 1.5 kHz: | about 85 Hz, |
| 4 kHz: | about 97 to at least 200 Hz. |
| (b) Normal Sleeping Adults | |
| 250 Hz: | about 85-95 Hz, |

| Auditory Signal | Modulation Frequency |
|---|---|
| 500 Hz: | about 85-95 Hz, |
| 1 kHz: | about 95 Hz, |
| 2 kHz: | about 105-160 Hz, |
| 4 kHz: | about 120 to at least 190 Hz. |
| 2 kHz: | the range of 80-115 Hz, substantially within the range of 85-195 Hz, |
| 4 kHz: | at least 85 to at least 200 Hz. |

9. A method of testing the hearing of a sleeping patient comprising the steps of supplying to said sleeping patient an auditory signal consisting of a carrier frequency which is periodically modulated such that the stimulus is at least substantially frequency specific, said auditory signal being presented for a sufficiently extended period of time to enable phase-locked, steady-state potentials to be evoked in the brain, sampling the brain potentials to determine whether phase-locking of said brain potentials to the modulated auditory signal has occurred, said auditory signals being periodically modulated at frequencies selected according to the following table:

| Auditory Signal | Modulation Frequency |
|---|---|
| (a) Normal Sleeping Neonates | |
| 500 Hz: | at least 70 Hz and substantially within the range of 70-140 Hz, |
| 1.5 kHz: | at least 75 Hz and substantially within the range of 75-165 Hz, |
| 4 kHz: | at least 75 to at least 200 Hz, |
| (b) Normal Sleeping Adults | |
| 250 Hz: | at least 70 Hz and substantially within the range of 75-130 Hz, |
| 500 Hz: | at least 75 Hz and substantially within the range of 75-180 Hz, |
| 1 kHz: | at least 75 Hz and substantially within the range of 75-200 Hz, |
| 2 kHz: | at least 75 to at least 200 Hz, |
| 4 kHz: | at least 75 to at least 200 Hz. |

10. The method of claim 9 wherein said frequency of modulation is selected according to the following table:

| Auditory Signal | Modulation Frequency |
|---|---|
| (a) Normal Sleeping Neonates | |
| 500 Hz: | substantially within the range of 70-95 Hz, |
| 1.5 kHz: | substantially within the range of 75-115 Hz, |
| 4 kHz: | at least 85 to at least 200 Hz, |
| (b) Normal Sleeping Adults | |
| 250 Hz: | substantially within the range of 80-115 Hz, |
| 500 Hz: | substantially within the range of 80-115 Hz, |
| 1 kHz: | substantially within the range of 80-115 Hz, |
| 2 kHz: | substantially within the range of 85-195 Hz, |
| 4 kHz: | at least 85 to at least 200 Hz. |

11. The method of claim 9 wherein said frequency of modulation is selected according to the following table:

| Auditory Signal | Modulation Frequency |
|---|---|
| (a) Normal Sleeping Neonates | |
| 500 Hz: | about 72 Hz, |
| 1.5 kHz: | about 85 Hz, |
| 4 kHz: | about 97 to at least 200 Hz, |
| (b) Normal Sleeping Adults | |
| 200 Hz: | about 85-95 Hz, |
| 500 Hz: | about 85-95 Hz, |
| 1 kHz: | about 95 Hz, |
| 2 kHz: | about 105-160 Hz, |
| 4 kHz: | about 120 to at least 190 Hz. |

12. An evoked response audiometer comprising means of supplying to a sleeping patient an auditory signal consisting of a carrier frequency which is periodically modulated such that the stimulus is at least substantially frequency specific, said auditory signal being presented for a sufficiently extended period of time to enable phase-locked steady-state potentials to be evoked in the brain, means for sampling the brain potential signals evoked by said signal, and means for analyzing said brain potentials to determine whether phase-locking of said brain potentials to the modulated auditory signal has occurred, said auditory signal means being controlled so that said auditory signals are periodically modulated at frequencies of at least 70 Hz, the frequency of modulation being varied in a generally increasing manner for auditory signals of higher frequencies;
said sampling means comprising means for multiplying said brain potential signals by said modulation frequency waveform and its quadrature component and by the waveform of the second harmonic of the modulation frequency and its quadrature component to produce product waveforms;
means for low-pass filtering said product waveforms to provide a time window which samples the brain potential for a predetermined interval to provide a set of Fourier analysis samples containing amplitude and phase data in narrow bands centered on the modulation frequency and its second harmonic.

13. The audiometer of claim 12, wherein said analysing means further comprises means for analysing said Fourier analysis samples to extract mean values of the amplitudes and phase angles of said signals, means for extracting from said mean values of said phase angles the probabilities (P%) that the distributions of said phase angles could have occurred by chance, whereby the existence of said phase locking is determined.

14. The audiometer of claim 13, wherein said Fourier analysis is performed by filters operating according to an approximation of the Hanning function $[1-\cos(2\pi t/t_H)]/2$ where $t_H$ is the width of the same time window.

15. The audiometer of claim 14, wherein said sampling means further comprises:
a computer, wherein said time window has a width of approximately 64 cycles and the computer samples the signals every 32 cycles to provide sample overlap.

16. The audiometer of claim 15, wherein said probability P% is extracted according to the functions:

$$F(N) = \left\{ Q \times (2/N) \left[ \sum_{i=1}^{N} \cos \theta_i \right]^2 + \left[ \sum_{i=1}^{N} \sin \theta_i \right]^2 \right\}$$

where
Q is a constant $\leq 1.0$, being approximately 0.625,
N is the number of said samples,
$\theta_i$ are said phase angles, and
Probability P% = 100 exp. (−0.5027F).

17. A method of testing the hearing of a sleeping patient comprising the steps of:
supplying to said sleeping patient an auditory signal consisting of a carrier frequency which is periodically modulated at frequencies in excess of 70 Hz such that the stimulus is at least substantially frequency specific, said auditory signal being presented for a sufficiently extended period of time to enable phase-locked steady-state potentials to be evoked in the brain;
sampling the brain potential signals evoked by said signal;
analysing said brain potentials to determine whether phase-locking of said brain potentials to the modulated auditory signal has occurred, the frequency of modulation being varied in a generally increasing manner for auditory signals of higher frequencies;
multiplying said brain potential signals by said modulation frequency waveform and its quadrature component and by the second harmonic of the modulation frequency and its quadrature component to produce product waveforms;
low-pass filtering said product waveforms to provide a time window which samples the brain potential for a predetermined interval to provide sets of samples containing amplitude and phase data in narrow bands centered on the modulation frequency and its second harmonic, said low-pass filtering providing Fourier analysis of said product waveforms to produce mean values of the amplitude and phaseangles of said signals; and
extracting from said mean values of said phase values the probabilities P% that the distributions of said phase angles, could have occurred by chance, whereby the existence of said phase locking is determined.

18. The method of claim 17, wherein said probability P% is extracted according to the functions:

$$F(N) = \left\{ Q \times (2/N) \left[ \sum_{i=1}^{N} \cos \theta_i \right]^2 + \left[ \sum_{i=1}^{N} \sin \theta_i \right]^2 \right\}$$

where
Q is a constant $\leq 1.0$, being approximately 0.625,
N is the number of said samples,
$\theta i$ are said phase angles for said samples, and
Probability P% = 100 exp. (−0.5027F).

* * * * *